United States Patent
Zhou et al.

(10) Patent No.: US 9,468,764 B2
(45) Date of Patent: Oct. 18, 2016

(54) NERVE SIGNAL DIFFERENTIATION IN CARDIAC THERAPY

(71) Applicant: Medtronic, Inc., Minneapolis, MN (US)

(72) Inventors: Xiaochong Zhou, Woodbury, MN (US); John Edward Burnes, Coon Rapids, MN (US); Lilian Kornet, Maastricht (NL); Richard N. M. Cornelussen, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 31 days.

(21) Appl. No.: 14/165,239

(22) Filed: Jan. 27, 2014

(65) Prior Publication Data
US 2014/0142650 A1 May 22, 2014

Related U.S. Application Data

(62) Division of application No. 12/848,019, filed on Jul. 30, 2010, now Pat. No. 8,639,327.

(60) Provisional application No. 61/397,702, filed on Apr. 29, 2010.

(51) Int. Cl.
*A61N 1/365* (2006.01)
*A61N 1/36* (2006.01)

(52) U.S. Cl.
CPC ....... *A61N 1/36139* (2013.01); *A61N 1/36053* (2013.01); *A61N 1/36114* (2013.01); *A61N 1/36514* (2013.01)

(58) Field of Classification Search
CPC .......................... A61N 1/365; A61N 1/36514
See application file for complete search history.

(56) References Cited

U.S. PATENT DOCUMENTS

| | | |
|---|---|---|
| 3,674,013 A | 7/1972 | Polanyl |
| 3,804,098 A | 4/1974 | Friedman |
| 3,937,226 A | 2/1976 | Funke |
| 4,088,138 A | 5/1978 | Diack et al. |
| 4,088,140 A | 5/1978 | Rockland et al. |
| 4,161,952 A | 7/1979 | Kinney et al. |
| 4,176,660 A | 12/1979 | Mylrea et al. |
| 4,198,963 A | 4/1980 | Barkalow et al. |
| 4,303,075 A | 12/1981 | Heilman et al. |
| 4,304,239 A | 12/1981 | Perlin |
| 4,321,929 A | 3/1982 | Lemelson et al. |
| 4,332,259 A | 6/1982 | McCorkle, Jr. |

(Continued)

FOREIGN PATENT DOCUMENTS

| | | |
|---|---|---|
| AU | 199890156 | 3/1999 |
| AU | 779255 | 1/2001 |

(Continued)

OTHER PUBLICATIONS

US 6,184,239, 02/2001, Puskas (withdrawn)

(Continued)

*Primary Examiner* — Eric D. Bertram
(74) *Attorney, Agent, or Firm* — Carol F. Barry

(57) ABSTRACT

Methods of nerve signal differentiation, methods of delivering therapy using such nerve signal differentiation, and to systems and devices for performing such methods. Nerve signal differentiation may include locating two electrodes proximate nerve tissue and differentiating between efferent and afferent components of nerve signals monitored using the two electrodes.

5 Claims, 11 Drawing Sheets

(56) References Cited

U.S. PATENT DOCUMENTS

| | | |
|---|---|---|
| 4,351,330 A | 9/1982 | Scarberry |
| 4,354,497 A | 10/1982 | Kahn |
| 4,428,378 A | 1/1984 | Anderson et al. |
| 4,458,677 A | 7/1984 | McCorkle, Jr. |
| 4,485,813 A | 12/1984 | Anderson et al. |
| 4,535,774 A | 8/1985 | Olson |
| 4,548,203 A | 10/1985 | Tacker, Jr. et al. |
| 4,574,807 A | 3/1986 | Hewson et al. |
| 4,603,705 A | 8/1986 | Speicher et al. |
| 4,640,298 A | 2/1987 | Pless et al. |
| 4,671,295 A | 6/1987 | Abrams et al. |
| 4,715,367 A | 12/1987 | Crossley |
| 4,722,347 A | 2/1988 | Abrams et al. |
| 4,750,495 A | 6/1988 | Moore et al. |
| 4,753,244 A | 6/1988 | Landymore et al. |
| 4,919,147 A | 4/1990 | Reinhardt et al. |
| 4,928,688 A | 5/1990 | Mower |
| 4,929,688 A | 5/1990 | Allen et al. |
| 4,931,464 A | 6/1990 | Grover et al. |
| 4,951,667 A | 8/1990 | Markowitz et al. |
| 4,952,586 A | 8/1990 | Morris et al. |
| 4,960,133 A | 10/1990 | Hewson |
| 4,969,463 A | 11/1990 | Dahl et al. |
| 5,003,991 A | 4/1991 | Takayama et al. |
| 5,007,893 A | 4/1991 | Row |
| 5,014,698 A | 5/1991 | Cohen |
| 5,024,228 A | 6/1991 | Goldstone et al. |
| 5,025,807 A | 6/1991 | Zabara |
| 5,036,848 A | 8/1991 | Hewson |
| 5,044,367 A | 9/1991 | Endres et al. |
| 5,050,600 A | 9/1991 | Parks |
| 5,052,390 A | 10/1991 | Hewson |
| 5,056,519 A | 10/1991 | Vince |
| 5,056,532 A | 10/1991 | Hull et al. |
| 5,117,822 A | 6/1992 | Laghi |
| 5,117,828 A | 6/1992 | Metzger et al. |
| 5,125,406 A | 6/1992 | Goldstone et al. |
| 5,127,407 A | 7/1992 | Tan |
| 5,129,392 A | 7/1992 | Bardy et al. |
| 5,154,170 A | 10/1992 | Bennett et al. |
| 5,154,172 A | 10/1992 | Terry, Jr. et al. |
| 5,156,149 A | 10/1992 | Hudrlik |
| 5,156,151 A | 10/1992 | Imran |
| 5,174,289 A | 12/1992 | Cohen |
| 5,178,149 A | 1/1993 | Imburgia et al. |
| 5,179,950 A | 1/1993 | Stanislaw |
| 5,179,952 A | 1/1993 | Buinevicius et al. |
| 5,186,170 A | 2/1993 | Varrichio et al. |
| 5,188,104 A | 2/1993 | Wernicke et al. |
| 5,199,428 A | 4/1993 | Obel et al. |
| 5,203,326 A | 4/1993 | Collins |
| 5,205,285 A | 4/1993 | Baker, Jr. |
| 5,215,086 A | 6/1993 | Terry, Jr. et al. |
| 5,231,988 A | 8/1993 | Wernicke et al. |
| 5,235,980 A | 8/1993 | Varrichio et al. |
| 5,243,980 A | 9/1993 | Mehra |
| 5,263,480 A | 11/1993 | Wernicke et al. |
| 5,265,603 A | 11/1993 | Hudrlik |
| 5,265,623 A | 11/1993 | Kroll et al. |
| 5,267,560 A | 12/1993 | Cohen |
| 5,269,298 A | 12/1993 | Adams et al. |
| 5,269,303 A | 12/1993 | Wernicke et al. |
| 5,282,468 A | 2/1994 | Klepinski |
| 5,284,146 A | 2/1994 | Czar et al. |
| 5,292,338 A | 3/1994 | Bardy |
| 5,299,569 A | 4/1994 | Wernicke et al. |
| 5,304,120 A | 4/1994 | Crandell et al. |
| 5,304,206 A | 4/1994 | Baker, Jr. et al. |
| 5,304,220 A | 4/1994 | Maginot |
| 5,306,293 A | 4/1994 | Zacouto |
| 5,315,995 A | 5/1994 | Rivers |
| 5,320,642 A | 6/1994 | Scherlag |
| 5,330,507 A | 7/1994 | Schwartz |
| 5,330,515 A | 7/1994 | Rutecki et al. |
| 5,334,221 A | 8/1994 | Bardy |
| 5,335,657 A | 8/1994 | Terry, Jr. et al. |
| 5,354,318 A | 10/1994 | Taepke |
| 5,356,425 A | 10/1994 | Bardy et al. |
| 5,365,926 A | 11/1994 | Desai |
| 5,379,765 A | 1/1995 | Kajiwara et al. |
| 5,403,356 A | 4/1995 | Hill et al. |
| 5,411,529 A | 5/1995 | Hudrlik |
| 5,411,531 A | 5/1995 | Hill et al. |
| 5,417,713 A | 5/1995 | Cohen |
| 5,423,877 A | 6/1995 | Mackey |
| 5,456,254 A | 10/1995 | Pietroski et al. |
| 5,458,625 A | 10/1995 | Kendall |
| 5,476,485 A | 12/1995 | Weinberg et al. |
| 5,501,702 A | 3/1996 | Plicchi et al. |
| 5,501,703 A | 3/1996 | Holsheimer et al. |
| 5,507,784 A | 4/1996 | Hill et al. |
| 5,514,161 A | 5/1996 | Limousin |
| 5,522,853 A | 6/1996 | Kroll |
| 5,522,854 A | 6/1996 | Ideker et al. |
| 5,531,776 A | 7/1996 | Ward et al. |
| 5,540,730 A | 7/1996 | Terry, Jr. |
| 5,540,732 A | 7/1996 | Testerman |
| 5,545,186 A | 8/1996 | Olson et al. |
| 5,549,655 A | 8/1996 | Erickson |
| 5,571,150 A | 11/1996 | Wernicke et al. |
| 5,578,061 A | 11/1996 | Stroetmann et al. |
| 5,584,867 A | 12/1996 | Limousin et al. |
| 5,611,350 A | 3/1997 | John |
| 5,620,468 A | 4/1997 | Mongeon et al. |
| 5,632,267 A | 5/1997 | Hognelid et al. |
| 5,651,378 A | 7/1997 | Matheny et al. |
| 5,656,420 A | 8/1997 | Chien |
| 5,658,318 A | 8/1997 | Stroetmann et al. |
| 5,662,689 A | 9/1997 | Elsberry et al. |
| 5,668,117 A | 9/1997 | Shapiro |
| 5,674,259 A | 10/1997 | Gray |
| 5,683,429 A | 11/1997 | Mehra |
| 5,690,681 A | 11/1997 | Geddes et al. |
| 5,700,282 A | 12/1997 | Zabara |
| 5,707,400 A | 1/1998 | Terry, Jr. et al. |
| 5,713,924 A | 2/1998 | Min et al. |
| 5,713,929 A | 2/1998 | Hess et al. |
| 5,720,768 A | 2/1998 | Verboven-Nelissen |
| 5,755,682 A | 5/1998 | Knudson et al. |
| 5,782,874 A | 7/1998 | Loos |
| 5,791,187 A | 8/1998 | Chang |
| 5,792,187 A | 8/1998 | Adams |
| 5,792,203 A | 8/1998 | Schroeppel |
| 5,797,970 A | 8/1998 | Pouvreau |
| 5,799,661 A | 9/1998 | Boyd et al. |
| 5,824,021 A | 10/1998 | Rise |
| 5,836,994 A | 11/1998 | Bourgeois |
| 5,840,076 A | 11/1998 | Swanson et al. |
| 5,843,133 A | 12/1998 | Routh et al. |
| 5,846,263 A | 12/1998 | Peterson et al. |
| 5,846,264 A | 12/1998 | Andersson et al. |
| 5,855,592 A | 1/1999 | McGee et al. |
| 5,865,838 A | 2/1999 | Obel et al. |
| 5,874,420 A | 2/1999 | Pelleg |
| 5,876,422 A | 3/1999 | van Groeningen |
| 5,889,033 A | 3/1999 | Kaminski |
| 5,893,881 A | 4/1999 | Elsberry et al. |
| 5,893,882 A | 4/1999 | Peterson et al. |
| 5,902,324 A | 5/1999 | Thompson et al. |
| 5,913,876 A | 6/1999 | Taylor et al. |
| 5,916,239 A | 6/1999 | Geddes et al. |
| 5,928,272 A | 7/1999 | Adkins et al. |
| 5,964,789 A | 10/1999 | Karsdon |
| 5,971,911 A | 10/1999 | Wilk |
| 5,977,408 A | 11/1999 | Levin et al. |
| 5,978,700 A | 11/1999 | Nigam |
| 5,991,656 A | 11/1999 | Olson et al. |
| 5,995,872 A | 11/1999 | Bourgeois |
| 5,998,386 A | 12/1999 | Feldman |
| 6,006,134 A | 12/1999 | Hill et al. |
| 6,007,559 A | 12/1999 | Arkans |
| 6,014,588 A | 1/2000 | Fitz |
| 6,018,682 A | 1/2000 | Rise |
| 6,042,538 A | 3/2000 | Puskas |

(56) References Cited

U.S. PATENT DOCUMENTS

| | | |
|---|---|---|
| 6,043,273 A | 3/2000 | Duhaylongsod |
| 6,060,454 A | 5/2000 | Duhaylongsod |
| 6,073,048 A | 6/2000 | Kieval et al. |
| 6,087,394 A | 7/2000 | Duhaylongsod |
| 6,091,988 A | 7/2000 | Warman et al. |
| 6,101,412 A | 8/2000 | Duhaylongsod |
| 6,103,722 A | 8/2000 | Schultz et al. |
| 6,127,410 A | 10/2000 | Duhaylongsod |
| 6,134,470 A | 10/2000 | Hartlaub |
| 6,141,589 A | 10/2000 | Duhaylongsod |
| 6,141,590 A | 10/2000 | Renirie et al. |
| 6,167,305 A | 12/2000 | Cammilli et al. |
| 6,185,459 B1 | 2/2001 | Mehra et al. |
| 6,221,851 B1 | 4/2001 | Feldman |
| 6,234,985 B1 | 5/2001 | Lurie et al. |
| 6,253,108 B1 | 6/2001 | Rosborough et al. |
| 6,256,537 B1 | 7/2001 | Stoop et al. |
| 6,259,947 B1 | 7/2001 | Olson et al. |
| 6,266,564 B1 | 7/2001 | Hill et al. |
| 6,272,380 B1 | 8/2001 | Warman et al. |
| 6,299,564 B1 | 10/2001 | Gessler et al. |
| 6,303,293 B1 | 10/2001 | Patterson et al. |
| 6,304,777 B1 | 10/2001 | Ben-Haim et al. |
| 6,381,499 B1 | 4/2002 | Taylor et al. |
| 6,393,316 B1 | 5/2002 | Gillberg et al. |
| 6,414,018 B1 | 7/2002 | Duhaylongsod |
| 6,429,217 B1 | 8/2002 | Puskas |
| 6,438,421 B1 | 8/2002 | Stahmann et al. |
| 6,442,429 B1 | 8/2002 | Hill et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,532,388 B1 | 3/2003 | Hill et al. |
| 6,537,540 B1 | 3/2003 | Burstein et al. |
| 6,542,774 B2 | 4/2003 | Hill et al. |
| 6,554,781 B1 | 4/2003 | Carter et al. |
| 6,572,895 B2 | 6/2003 | Smith et al. |
| 6,587,719 B1 | 7/2003 | Barrett et al. |
| 6,609,025 B2 | 8/2003 | Barrett et al. |
| 6,611,713 B2 | 8/2003 | Schauerte |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,656,960 B2 | 12/2003 | Puskas |
| 6,690,973 B2 | 2/2004 | Hill et al. |
| 6,711,436 B1 | 3/2004 | Duhaylongsod |
| 6,718,208 B2 | 4/2004 | Hill et al. |
| 6,721,603 B2 | 4/2004 | Zabara et al. |
| 6,731,978 B2 | 5/2004 | Olson et al. |
| 6,735,471 B2 | 5/2004 | Hill et al. |
| 6,738,667 B2 | 5/2004 | Deno et al. |
| 6,778,854 B2 | 8/2004 | Puskas |
| RE38,654 E | 11/2004 | Hill et al. |
| RE38,705 E | 2/2005 | Hill et al. |
| 6,850,801 B2 | 2/2005 | Kieval et al. |
| 6,889,077 B2 | 5/2005 | Bornzin et al. |
| 6,904,318 B2 | 6/2005 | Hill et al. |
| 6,912,419 B2 | 6/2005 | Hill et al. |
| 7,024,238 B2 | 4/2006 | Bergethon |
| 7,138,607 B2 | 11/2006 | Wang et al. |
| 7,139,607 B1 | 11/2006 | Shelchuk |
| 7,200,438 B2 | 4/2007 | Euler |
| 7,225,019 B2 | 5/2007 | Jahns et al. |
| 7,231,254 B2 | 6/2007 | DiLorenzo |
| 7,245,967 B1 | 7/2007 | Shelchuk |
| 7,269,457 B2 | 9/2007 | Shafer et al. |
| 7,299,091 B2 | 11/2007 | Barrett et al. |
| 7,321,793 B2 | 1/2008 | Ben Ezra et al. |
| 7,493,161 B2 | 2/2009 | Libbus et al. |
| 7,499,748 B2 | 3/2009 | Moffitt et al. |
| 7,509,166 B2 | 3/2009 | Libbus |
| 7,542,800 B2 | 6/2009 | Libbus et al. |
| 7,548,780 B2 | 6/2009 | Libbus et al. |
| 7,555,341 B2 | 6/2009 | Moffitt et al. |
| 7,555,345 B2 | 6/2009 | Wahlstrand et al. |
| 7,587,238 B2 | 9/2009 | Moffit et al. |
| 7,643,875 B2 | 1/2010 | Heil, Jr. et al. |
| 7,711,421 B2 | 5/2010 | Shafer et al. |
| 7,826,899 B1 | 11/2010 | Ryu et al. |
| 7,840,278 B1 | 11/2010 | Puskas |
| 8,012,189 B1* | 9/2011 | Webb et al. ............... 607/89 |
| 8,032,215 B2 | 10/2011 | Libbus et al. |
| 8,036,741 B2 | 10/2011 | Jahns et al. |
| 8,036,756 B2 | 10/2011 | Swoyer et al. |
| 8,406,868 B2 | 3/2013 | Buschman et al. |
| 8,423,134 B2 | 4/2013 | Buschman et al. |
| 8,571,653 B2 | 10/2013 | Ben-David et al. |
| 8,620,425 B2 | 12/2013 | Zhou et al. |
| 8,639,327 B2 | 1/2014 | Zhou et al. |
| 8,706,223 B2 | 4/2014 | Zhou et al. |
| 8,718,763 B2 | 5/2014 | Zhou et al. |
| 8,725,259 B2 | 5/2014 | Kornet et al. |
| 8,781,582 B2 | 7/2014 | Ziegler et al. |
| 8,781,583 B2 | 7/2014 | Cornelussen et al. |
| 8,888,699 B2 | 11/2014 | Buschman et al. |
| 2001/0049543 A1 | 12/2001 | Kroll |
| 2002/0035335 A1 | 3/2002 | Schauerte |
| 2002/0049478 A1 | 4/2002 | Ding et al. |
| 2002/0072782 A1 | 6/2002 | Osorio et al. |
| 2002/0107553 A1 | 8/2002 | Hill et al. |
| 2002/0198570 A1 | 12/2002 | Puskas |
| 2002/0198571 A1 | 12/2002 | Puskas |
| 2003/0045909 A1 | 3/2003 | Gross et al. |
| 2003/0060857 A1 | 3/2003 | Perrson et al. |
| 2003/0074039 A1 | 4/2003 | Puskas |
| 2003/0187479 A1 | 10/2003 | Thong |
| 2003/0216775 A1 | 11/2003 | Hill et al. |
| 2003/0216790 A1 | 11/2003 | Hill et al. |
| 2004/0024422 A1 | 2/2004 | Hill et al. |
| 2004/0059383 A1 | 3/2004 | Puskas |
| 2004/0111118 A1 | 6/2004 | Hill et al. |
| 2004/0162584 A1 | 8/2004 | Hill et al. |
| 2004/0172075 A1 | 9/2004 | Shafer et al. |
| 2004/0186517 A1 | 9/2004 | Hill et al. |
| 2004/0186531 A1 | 9/2004 | Jahns et al. |
| 2004/0193231 A1 | 9/2004 | David et al. |
| 2004/0199209 A1 | 10/2004 | Hill et al. |
| 2004/0210261 A1 | 10/2004 | King et al. |
| 2004/0220631 A1 | 11/2004 | Burnes et al. |
| 2005/0096707 A1 | 5/2005 | Hill et al. |
| 2005/0119704 A1 | 6/2005 | Peters et al. |
| 2005/0143412 A1 | 6/2005 | Puskas |
| 2005/0197675 A1 | 9/2005 | David et al. |
| 2006/0074450 A1 | 4/2006 | Boveja et al. |
| 2006/0095081 A1 | 5/2006 | Zhou et al. |
| 2006/0106429 A1 | 5/2006 | Libbus et al. |
| 2006/0135998 A1* | 6/2006 | Libbus et al. ............... 607/2 |
| 2006/0173494 A1 | 8/2006 | Armstrong et al. |
| 2006/0206158 A1 | 9/2006 | Wu et al. |
| 2006/0206159 A1 | 9/2006 | Moffitt et al. |
| 2006/0224202 A1 | 10/2006 | Moffitt et al. |
| 2006/0271115 A1 | 11/2006 | Ben-Ezra et al. |
| 2006/0293712 A1 | 12/2006 | Kieval et al. |
| 2007/0021792 A1 | 1/2007 | Kieval et al. |
| 2007/0021796 A1 | 1/2007 | Kieval et al. |
| 2007/0021799 A1 | 1/2007 | Kieval et al. |
| 2007/0043400 A1 | 2/2007 | Donders et al. |
| 2007/0083242 A1 | 4/2007 | Mazgalev et al. |
| 2007/0106337 A1 | 5/2007 | Errico et al. |
| 2007/0129764 A1 | 6/2007 | Burnes |
| 2007/0260283 A1 | 11/2007 | Li |
| 2007/0299476 A1* | 12/2007 | Park et al. ............... 607/9 |
| 2008/0058872 A1 | 3/2008 | Brockway et al. |
| 2008/0058874 A1 | 3/2008 | Westlund et al. |
| 2008/0091240 A1 | 4/2008 | Ben-David et al. |
| 2008/0234780 A1 | 9/2008 | Smith et al. |
| 2008/0269819 A1 | 10/2008 | Zhou |
| 2008/0300640 A1 | 12/2008 | Mazgalev et al. |
| 2009/0005845 A1 | 1/2009 | David et al. |
| 2009/0234408 A1 | 9/2009 | Moffitt et al. |
| 2009/0306491 A1 | 12/2009 | Haggers |
| 2010/0036447 A1 | 2/2010 | Zhang et al. |

(56) References Cited

U.S. PATENT DOCUMENTS

| | | | |
|---|---|---|---|
| 2010/0114208 A1 | 5/2010 | Donofrio et al. |
| 2010/0286740 A1 | 11/2010 | Libbus et al. |
| 2010/0312299 A1 | 12/2010 | Maciejewski et al. |
| 2011/0004262 A1 | 1/2011 | Bianchi et al. |
| 2011/0270332 A1 | 11/2011 | Buschman et al. |
| 2011/0270342 A1 | 11/2011 | Buschman et al. |
| 2011/0270343 A1 | 11/2011 | Buschman et al. |
| 2012/0029586 A1 | 2/2012 | Kumar et al. |
| 2012/0029587 A1 | 2/2012 | Zhou et al. |
| 2012/0029600 A1 | 2/2012 | Zhou et al. |
| 2012/0078132 A1 | 3/2012 | Zdeblick et al. |
| 2012/0185007 A1 | 7/2012 | Ziegler et al. |
| 2012/0185008 A1 | 7/2012 | Zhou et al. |
| 2012/0185009 A1 | 7/2012 | Kornet et al. |
| 2012/0185010 A1 | 7/2012 | Zhou et al. |
| 2012/0185011 A1 | 7/2012 | Cornelussen et al. |
| 2014/0114163 A1 | 4/2014 | Zhou et al. |
| 2014/0316486 A1 | 10/2014 | Zhou et al. |
| 2014/0324115 A1 | 10/2014 | Ziegler et al. |

FOREIGN PATENT DOCUMENTS

| | | |
|---|---|---|
| CA | 2310183 | 8/1998 |
| CA | 2 376 903 A1 | 1/2001 |
| DE | 2811325 | 9/1979 |
| EP | 0440111 A2 | 8/1991 |
| EP | 0547734 A2 | 6/1993 |
| EP | 0562408 A1 | 9/1993 |
| EP | 0589252 A2 | 3/1994 |
| EP | 0756507 B1 | 2/1999 |
| EP | 1 005 337 | 3/1999 |
| EP | 1 051 168 | 11/2000 |
| EP | 1181947 A2 | 2/2002 |
| EP | 1426078 A1 | 6/2004 |
| EP | 1 005 337 B1 | 5/2005 |
| EP | 1 051 168 B1 | 3/2006 |
| EP | 1870129 A1 | 12/2007 |
| JP | 2000507363 | 8/1998 |
| JP | 2001505980 | 6/2000 |
| MX | PA00002043 | 3/2004 |
| WO | WO 92/11064 A1 | 7/1992 |
| WO | WO 97/40885 A1 | 2/1997 |
| WO | WO 97/13550 A1 | 4/1997 |
| WO | WO 99/00057 A1 | 1/1999 |
| WO | WO 99/07354 A2 | 2/1999 |
| WO | WO 99/09971 A1 | 3/1999 |
| WO | WO 99/09973 A1 | 3/1999 |
| WO | WO 99/63926 A2 | 12/1999 |
| WO | WO 00/01306 A1 | 1/2000 |
| WO | WO 00/09206 A1 | 2/2000 |
| WO | WO 01/00273 A1 | 2/2001 |
| WO | WO 01/89526 A1 | 11/2001 |
| WO | WO 02/26320 A1 | 4/2002 |
| WO | WO 03/103484 A2 | 12/2003 |
| WO | WO 03/103484 A3 | 4/2004 |
| WO | WO 2007/142563 A1 | 12/2007 |
| WO | WO 2008/144125 A1 | 11/2008 |

OTHER PUBLICATIONS

Adams, "Gains in Pain Research: Past Failures Push Investigators to be More Innovative in their Treatment Approaches," *The Scientist*, Dec. 15, 2003; 17(24); 6 pages.

Agnew et al., "Considerations for Safety with Chronically Implanted Nerve Electrodes," *Epilepsia*, 1990; 31(Suppl. 2):S27-S32.

American Heart Association definition of Atrial or Supraventricular Tachycardia, http://www.heart.org/HEARTORG/Conditions/Arrhythmia/AboutArrhythmia/Tachycardia_UCM_302018_Article.jsp. Content last reviewed May 13, 2012. Copyright 2013. 2 pages.

Ando et al., "Efferent Vagal Nerve Stimulation Protects Heart Against Ischemia-Induced Arrhythmias by Preserving Connexin43 Protein," *Circulation*, 2005; 112:164-170.

Annegers et al., "Epilepsy, Vagal Nerve Stimulation by the NCP System, All-Cause Mortality, and Sudden, Unexpected, Unexplained Death," *Epilepsia*, 2000; 41(5):549-553.

"Atrial Fibrillation: Current Understandings and Research Imperatives," The National Heart, Lung, and Blood Institute Working Group on Atrial Fibrillation, *JACC*, Dec. 1993; 22(7):1830-1834.

Barwell et al., "The NIM-2 Nerve Integrity Monitor in Thyroid and Parathyroid Surgery," *British Journal of Surgery*, 1997; 84:854.

Beekwilder et al., "Overview of the Clinical Applications of Vagus Nerve Stimulation," *Journal of Clinical Neurophysiology*, Apr. 2010; 27(2):130-138.

Bell et al., "Intropic Response of the Left Ventricle to Changes in Heart Rate in Anesthetized Rabbits," *Can.J. Physiol. Pharmacol.*, 1987; 65(2):179-184.

Bennetti, "Direct Coronary Surgery with Saphenous Vein Bypass Without Either Cardiopulmonary Bypass or Cardiac Arrest," *J. Cardiovasc. Surg.*, 1985; 26:217-222.

Bennetti et al., "Use of Thoracoscopy and a Minimal Thoracotomy, in Mammary-Coronary Bypass to Left Anterior Descending Artery, Without Extracorporeal Circulation," *J. Cardiovasc. Surg.*, Apr. 1995; 36(2): 159- 161.

Ben-Menachem et al., "Vagus Nerve Stimulation for Treatment of Partial Seizures: 1. A Controlled Study of Effect on Seizures," *Epilepsia*, 1994; 35(3):616-626.

Besedovsky et al, "Immunoregulatory Feedback Between Interleukin-1 and Glucocorticoid Hormones," *Science*, Aug. 8, 1986; 233(4764):652-654.

Bianchi et al., "Endocardial Transcatheter Stimulation of the AV Node Fat Pad: Stabilization of Rapid Ventricular Rate Response During Atrial Fibrillation in Left Ventricular Failure" *Journal of Cardiovascular Electrophysiology*, Jan. 2009; 20(1):103-105. Epub Jul. 3, 2008.

Bilgutay et al. "Vagal Tuning—A New Concept in the Treatment of Supraventricular Arrhythmias, Angina Pectoris, and Heart Failure," Jul. 1968, *Journal of Thoracic and Cardiovascular Surgery*, vol. 56, No. 1, pp. 71-82.

Binks et al., "High Strength Stimulation of the Vagus Nerve in Awake Humans: a Lack of Cardiorespiratory Effects," *Respiration Physiology*, 2001; 127:125-133.

Bluemel et al., "Parasympathetic Postganglionic Pathways to the Sinoartrial Node," *Am. J. Physiol.*, 1990; 259(5 Pt 2):H1504-H1510.

Borovikova et al., "Role of Vagus Nerve Signaling in CNI-1493-Mediated Suppression of Acute Inflammation," *Autonomic Neuroscience: Basic and Clinical*, 2000; 85:141-147.

Borovikova et al., "Vagus Nerve Stimulation Attenuates the Systemic Inflammatory Response to Endotoxin," *Nature*, 2000; 405(6785):458-462.

Braunwald et al., "Carotid Sinus Nerve Stimulation in the Treatment of Angina Pectoris and Supraventricular Tachycardia," *California Medicine: The Western Journal of Medicine*, 1970; 112(3):41-50.

Bristow, "The Adrenergic Nervous System in Heart Failure," *The New Eng. J. of Med.*, Sep. 27, 1984; 311(13):850-851.

Brodde et al., "Cardiac Muscarinic Receptors Decrease with Age: In Vitro and In Vivo Studies," *Journal of Clinical Investigations*, Jan. 1998; 101(2):471-478.

Bufkin et al., "Controlled Intermittent Asystole: Parmacologic Potentiation of Vagal-Induced Asystole," *Ann.Thorac. Surg.*, 1998; 66:1185-1190.

Buschman et al., "Control of Heart Rate with Vagus Nerve Stimulation," 7th Annual Conference of the International Functional Electrical Stimulation Society (IFESS), Ljubijana, Slovenia, Jun. 25-29, 2002. Abstract not available.

Buschman et al., "Heart Rate Control Via Vagus Nerve Stimulation," *Neuromodulation*, Jul. 2006; 9(3):214-220.

Carlson et al., "Selective Stimulation of Parasympathetic Nerve Fibers to the Human Sinoatrial Node," *Circulation*, Apr. 1992; 85(4):1311-1317.

Carlsson et al., "Therapy of Atrial Fibrillation: Rhythm Control Versus Rate Control," *PACE*, May 2000; 23:891-903.

Chiou, "Efferent Vagal Innervation of the Canine Atria and Sinus and Atrioventricular Nodes: The Third Fat Pad" *Circulation*, 1997; 95:2573-2584.

(56) References Cited

OTHER PUBLICATIONS

Clarke et al., Cognitive Motor Function After Electrical Stimulation of the Vagus Nerve, *PACE*, Oct. 1992; 15(10 PartII):1603-1607.
Clarke et al., "Acute Effects of High Frequency Vagal Nerve Stimulation on Balance and Cognitive Motor Performance in Epilepsy: Three Case Study Reports," *PACE*, Oct. 1992; 15(10 PartII):1608-1613.
Clarke et al., "Electrostimulation Effects of the Vagus Nerve on Balance in Epilepsy," *PACE*, Oct. 1992; 15(10 PartII):1614-1630.
Cooper et al., "Neural Effects on Sinus Rate and Atrioventricular Conduction Produced by Electrical Stimulation from a Transvenous Electrode Catheter in the Canine Right Pulmonary Artery," *Circulation Research*, Jan. 1980; 46(1):48-57.
Daubert et al., "Inaproptiate Implantable Cardioverter-Defibrillator Shocks in MADIT II: Frequency, Mechanisms, Predictors, and Survival Impact," *J. Am. Coll. Cardiol.*, 2008; 51:1357-1365.
DiMarco et al., "Adenosine: Electrophysiologic Effects and Therapeutic Use for Terminating Paroxysmal Supraventricular Tachycardia," *Circulation*, Dec. 1983; 68(6):1254-1263.
Dipiro et al., Editor, "Pharmacotherapy: A Pathophysiologic Approach," 1989; 153-157.
Diwan et al., "Inflammatory Mediators and the Failing Heart: A Translational Approach," *Cur. Mol. Med.*, 2003; 3(2):161-182.
Donaldson et al., "Velocity-selective recording using multi-electrode nerve cuffs," 7$^{th}$ Annual Conference of the International Functional Electrical Stimulation Society (IFESS), Ljubijana, Slovenia, Jun. 25-29, 2002; 5 pgs.
Duhaylongsod et al., "Controlled Ventricular Asystole with Surgeon-Actuated Pacing for Off-Pump Coronary Artery Bypass Grafting: A Proposed Surgical Method," Presentation Summary, Presented at International Society for Minimally Invasive Cardiac Surgery Annual Meeting, Jun. 25, 1998, Minneapolis, MN, 1 page.
Eckberg, "The Human Respiratory Gate" *J. Physiol.*, 2003; 548. 2:339-352.
Espinosa et al., "Revision and Removal of Stimulating Electrodes Following Long-Term Therapy with the Vagus Nerve Stimulator," *Surgical Neurology*, 1999; 51: 659-664.
Fanning et al., "Reoperative Coronary Artery Bypass Grafting Without Cardiopulmonary Bypass," *Ann. Thorac. Surg.*, Feb. 1993; 55(2):486-489.
Finkel et al., "Negative Inotropic Effects of Cytokines on the Heart Mediated by Nitric Oxide," *Science*, Jul. 17, 1992; 257(5068):387-389.
Fleshner et al., "Thermogenic and Corticosterone Responses to Intravenous Cytokines (IL-1β and TNF-α) are Attenuated by Subdiaphragmatic Vagotomy," *J. of Neuroimmunology*, 1998; 86:134-141.
Freilich et al., "Adenosine and its Cardiovascular Effects," *American Heart Journal*, May 1992; 123(5):1324-1328.
Garcia-Perez et al., "Effect of Stimulating Non-myelinated Vagal Axons on Atrio-ventricular Conduction and Left Ventricular Function in Anaesthetized Rabbits," *Autonomic Neuroscience: Basic and Clinical*, 2001; 86:183-191.
Garnett et al., "Regional Cerebral Blood Flow in Man Manipulated by Direct Vagal Stimulation," *PACE*, Oct. 1992; 15(10 PartII):1579-1580.
Gaykema et al., "Subdiaphragmatic Vagotomy Suppresses Endotoxin-Induced Activation of Hypothalamic Corticotropin-Releasing Hormone Neurons and ACTH Secretion," *Endocrinology*, Oct. 1995; 136(10):4717-4720.
George et al., "Vagus Nerve Stimulation for Treatment of Partial Seizures: 3. Long-Term Follow-Up on First 67 Patients Exiting a Controlled Study," *Epilepsia*, 1994; 35(3):637-643.
Gorman et al., "How New Heart-Scanning Technology Could Save Your Life," *Time*, Sep. 5, 2005; 8 pages.
Guarini et al., "Efferent Vagal Fibre Stimulation Blunts Nuclear Factor-kB Activation and Protects Against Hypovolemic Hemorrhagic Shock," *Circulation*, Mar. 4, 2003; 107(8):1189-1194.

Gulick et al., "Interleukin 1 and Tumor Necrosis Factor Inhibit Cardiac Myocyte β-adrenergic Responsiveness," *Proc. Natl. Acad. Sci. USA*, Sep. 1989; 86(17):6753-6757.
Gupta, "Suppression of Paroxysmal Atrial Fibrillation by Pacing," *Indian Pacing and Electrophysiology Journal*, 2003; 3(2):45-46.
Hageman et al., "Direct and Reflex Cardiac Bradydysrhythmias From Small Vagal Nerve Stimulations," *Am. Heart J.*, Mar. 1975; 89(3):338-348 (Abstract only).
Hammond et al., "Vagus Nerve Stimulation in Humans: Neurophysiological Studies and Electrophysiological Monitoring," *Epilepsia*, 1990; 31(Suppl. 2):S51-S59.
Harvey et al., "Radiofrequency Catheter Ablation for Atrial Fibrillation," *Coronary Artery Disease*, 1995; 6:115-120.
Henning et al., "Vagal Nerve Stimulation Increases Right Ventricular Contraction and Relaxation and Heart Rate," *Cardiovascular Research*, 1996; 32:846-853.
Hirota et al., "Loss of gp130 Cardiac Muscle Cell Survival Pathway is a Critical Event in the Onset of Heart Failure during Biomechanical Stress," *Cell*, 1999; 97:189-198.
Holder et al., "Treatment of Refractory Partial Seizures: Preliminary Results of a Controlled Study," *PACE*, Oct. 1992; 15(10 PartII):1557-1571.
Israel et al., "Atrial Pacing in the Prevention of Paroxysmal Atrial Fibrillation: First Results of a New Combined Algorithm," *PACE*, Nov. 2000, Part II; 23:1888-1890.
Jalife et al., "Desensitization of the Cholinergic Receptor at the Sinoatrial Cell of the Kitten," *Am. J. Physiol.*, 1980; 238(4):H439-448.
Jones, "Vagal Control of the Rat Heart," *Exp. Physiol.*, Nov. 2001; 86(6):797-801.
Kale et al., "Atrial Septal Pacing in the Prevention of Paroxysmal Atrial Fibrillation Refractory to Antiarrhythmic Drugs," *International Journal of Cardiology*, 2002; 82:167-175.
Kamath et al., "Neurocardiac Responses to Vagoafferent Electrostimulation in Humans," *PACE*, Oct. 1992; 15(10 PartII):1581-1587.
Kandel et al., editors, Principles of Neural Science, Fourth Edition, McGraw-Hill, New York, 2000. Title page, copyright page and table of contents, 29 pgs.
Khanna et al., "Coronary Artery Surgery with Induced Temporary Asystole and Intermittent Ventricular Pacing: An Experimental Study," *Cardiovascular Surgery*, Apr. 1996, 4(2):231-236.
Klassen et al., "Coronary Venous Pressure and Flow: Effects of Vagal Stimulation, Aortic Occulsion and Vasodialators," *Can. J. Physiol. Pharmacol.*, May 1984; 62(5):531,538.
Kornet et al., "Stimulation of the Intra-Cardiac Vagal Nerves Innervating the AV-Node to Control Ventricular Rate During AF: Specificity, Parameter Optimization and Chronic Use up to 3 Months," *J. Interv. Card. Electrophysiol.*, Jan. 2012; 33(1):7-18. Published online Oct. 4, 2011.
Krown et al., "Tumor Necrosis Factor Alpha-Induced Apoptosis in Cardiac Myocytes: Involvement of the Sphingolipid Signaling Cascade in Cardiac Cell Death," *J. Clin. Invest.*, 1996; 98(12):2854-2865.
Lagi et al., "Age-Related Changes of Cardiac Parasympathetic Modulation After Vasovagal Syncope," *American Journal of Cardiology*, Mar. 15, 1999; 83:977-980.
Laperche et al., "Potential Interests of Heart Rate Lowering Drugs" *Heart*, 1999; 81:336-341.
Levine et al., "Pacing for the Suppression of Paroxysmal Atrial Fibrillation in an 87-year-old Patient," *Indian Pacing and Electrophysiology Journal*, 2003; 3(2):88-90.
Levy et al., "Autonomic Control of Cardiac Pacemaker Activity and Atrioventricular Transmission," *Journal of Applied Physiology*, Oct. 1969; 27(4):465-470.
Levy et al., "Parasympathetic Control of the Heart," Chapter 4, Nervous Control of Cardiovascular Function, Oxford University Press, New York, 1984, pp. 68-94.
Li et al., "Myocardial Extracellular Matrix Remodeling in Transgenic Mice Overexpressing Tumor Necrosis Factor a can be modulated by Anti-Tumor Necrosis Factor A Therapy," *PNAS*, Nov. 7, 2000; 97(23):12746-12751.

(56) References Cited

OTHER PUBLICATIONS

Li et al, "Vagal Nerve Stimulation Markedly Improves Long-Term Survival after Chronic Heart Failure in Rats," *Circulation*, 2004; 109:120-124.
Lisman et al., "The Role of Tumor Necrosis Factor Alpha Blockade in the Treatment of Congestive Heart Failure," *CHF*, Sep./Oct. 2002; pp. 275-279.
Lockard et al., "Feasibility and Safety of Vagal Stimulation in Monkey Model," *Epilepsia*, 1990; 31(Supp. 2):S20-S26.
Loeb et al., "Sensitivity Differences of SA and AV Node to Vagal Stimulation: Attenuation of Vagal Effects at SA Node," *Am. J. Physiol.*, Nov. 1981; 241(5):H684-H690.
McGregor et al., "Proteomics of Heart Disease," *Human Molecular Genetics*, Oct. 15, 2003; 12(Review Issue 2):R135-R144.
Maloney et al., "A New Method for Intraoperative Recurrent Laryngeal Nerve Monitoring," *ENT Journal*, 1994; 73(1):30-33.
Mann, "Mechanisms and models in Heart Failure—A Combinatorial Approach," *Circulation*, Aug. 31, 1999; 100(9):999-1008.
Mann et al., "New Therapeutics for Chronic Heart Failure," *Annu. Rev. Med.*, 2002; 53:59-74.
Martin et al., "Fade of Cardiac Responses During Tonic Vagal Stimulation," *Am. J. Physiol.*, 1982; 243(2):H219-H225.
Matheny et al., "Vagus Nerve Stimulation as a Method to Temporarily Slow or Arrest the Heart," Presented at the Second Utrecht MICABG Workshop, Oct. 4-5, 1996, Utrecht, Netherlands. Transcription of Presentation. *Annals of Thoracic Surgery*, Jun. 6, 1997; 63(6):528-529.
Matheny, "Techniques of Stabilization," Experiences in Minimally Invasive Surgery Conference, Jun. 19-21, 1997, Minneapolis, MN. Transcription of Presentation, 6 pages.
Mitchell, "The Role of Pacemaker and Defibrillator Therapy for the Treatment of Atrial Fibrillation," *Minerva Cardioangiologica*, Apr. 2004, 52(2):141-153.
Mohiuddin et al., "Safety of different Dosages of Intravenous Adenosine Used in Conjunction with Diagnostic Myocardial Imaging Techniques," *Pharmacotherapy*, Sep./Oct. 1993; 13(5):476-480.
Murgatroyd, "Pills and Pulses: Hybrid Therapy for Atrial Fibrillation," *Journal of Cardiovascular Electrophysiology*, Jan. 2002; 13(1) Suppl:S40-S46.
Nanthakumar et al., "Inappropriate Therapy from Atrial Fibrillation and Sinus Tachycardia in Automated Implantable Cardioverter Defibrillators," *American Heart Journal*, May 2000; 139(5):797-803.
Naritoku et al., "Chronic Vagus Nerve Stimulation Increases the Latency of the Thalamocortical Somatosensory Evoked Potential," *PACE*, Oct. 1992; 15(10 PartII): 1572-1578.
Nerheim et al., "Heart Failure and Sudden Death in Patients with Tachycardia-Induced Cardiomyopathy and Recurrent Tachycardia," *Circulation*, 2004; 110:247-252.
Nobrega et al., "Resting and Reflex Heart Rate Responses During Cholinergic Stimulation with Pyridostigmine in Humans," *Braz. J. Med. Biol. Res.*, Nov. 1996; 29(11):1461-1465 (Abstract Only).
Noonan, "And the Beat Goes on," *Newsweek*, Jul. 11, 2005, pp. 56-57.
Nunain et al., "Limitations and Late Complications of Third-Generation Automatic Cardioverter-Defibrillators," *Circulation*, 1995; 91:2204-2213.
Ogawa et al., "Acute Effects of Different Atrial Pacing Sites in Patients with Atrial Fibrillation: Comparison of Single Site and Biatrial Pacing," *PACE*, Oct. 2001; 24:1470-1478.
Okazawa et al., "Effect of Vagal Stimulations and Parenteral Acetylcholine on Canine Trachealis Muscle Shortening," *J. Appl. Physiol.*, 1992; 75(6):2463-2468, (Abstract Only).
Ordelman et al., "Average Reference Recording from the Vagal Nerve Reveals an Evoked Indirect Response" Proceedings of the 4th International IEEE EMBS Conference on Neural Engineering Antalya, Turkey, Apr. 29-May 2, 2009.
Ordelman et al., "An Evoked Indirect Response in the Cervical Vagal Nerve" 4th Annual Symposium of the IEEE-IMBS Benelux Chapter, Nov. 9-10, 2009, Enschede, The Netherlands; p. 28.
Ordelman et al., "An Indirect Component in the Evoked Compound Action Potential of the Vagal Nerve" *J. Neural. Eng.*, 2010; 7:1-9.
Ousdigian et al., "Continuous ICD Diagnostics Triage Patients for Urgent Intervention: Low vs. High Risk of Inappropriate Shocks for AF," Heart Rhythm Society Congress 2008, 29th Annual Scientific Sessions, May 14-17, 2008, San Francisco, CA.
Pavlov et al., "Central Muscarinic Cholinergic Regulation of the Systemic Inflammatory Response during Endotoxemia," *PNAS*, Mar. 28, 2006; 103(13):5219-5223.
Penry et al., "Prevention of Intractable Partial Seizures by Intermittent Vagal Stimulation in Humans: Preliminary Results," *Epilepsia*, 1990; 31(Suppl.2):S40-S43.
Pfister et al., "Coronary Artery Bypass Without Cardiopulmonary Bypass," *Ann. Thorac. Surg.*, Dec. 1992; 54(6):1085-1092.
Poller et al., "Age-Dependent Changes in Cardiac Muscarinic Receptor Function in Healthy Volunteers," *Journal of American College of Cardiology*, Jan. 1997; 29(1):187-193.
Poole et al., "Prognostic Importance of Defibrillator Shocks in Patients with Heart Failure," *New England Journal of Medicine*, Sep. 4, 2008, 359:1009-1017.
Puglisi et al., "Persistent Atrial Fibrillation Worsens Heart Rate Variability, Activity and Heart Rate, as Shown by a Continuous Monitoring by Implantable Biventricular Pacemakers in Heart Failure Patients," *Journal of Cardiovascular Electrophysiology*, Jul. 2008; 19(7):693-701.
Pulkki, "Cytokines and Cardiomyocyte Death," Annals of Medicine, 1997; 29:339-343.
Purefellner et al., "Accuracy of Atrial Tachyarrhythmia Detection in Implantable Devices with Arrhythmia Therapies," *PACE*, Jul. 2004; 27:983-992.
Puskas, Declaration/Clarification of John D. Puskas, MD, dated Oct. 11, 2005, 7 pgs.
Ramsay et al., "Vagus Nerve Stimulation for Treatment of Partial Seizures: 2. Safety, Side Effects, and Tolerability," *Epilepsia*, 1994; 35(3):627-636.
Randall et al., "Functional Anatomy of the Cardiac Efferent Innervation," *Neurocardiology*, 1988; pp. 3-24.
Reid, "Surgical Technique for Implantation of the Neurocybernetic Prosthesis," *Epilepsia*, 1990; 31(Suppl. 2):S38-S39.
Ricci et al., "Efficacy of a Dual Chamber Defibrillator with Atrial Antitachycardia Functions in Treating Spontaneous Atrial Tachyarrhythmias in Patients with Life-Threatening Ventricular Tachyarrhythmias" *European Heart Journal*, 2002; 23:14711479.
Rieger et al., "Experimental determination of compound action potential direction and propagation velocity from multi-electrode nerve cuffs" *Medical Engineering & Physics*, 2004; 26: 531-534.
Rosenqvist et al., "Relative Importance of Activation Sequence Compared to Atrioventricular Synchrony in Left Ventricular Function," *The American Journal of Cardiology*, Jan. 15, 1991; 67:148-156.
Rossi et al., "Post-Operative Atrial Fibrillation Management by Selective Epicardial Vagal Fat Pad Stimulation" *J. Interv. Card. Electrophysiol.*, 2009; 24:37-45.
Rossi et al., "Vagal Tone Augmentation to the Atrioventricular Node in Humans: Efficacy and Safety of Burst Endocardial Stimulation" *Heart Rhythm*, May 2010; 7(5):683-689.
Rossi et al., "Endocardial Vagal Atrioventricular Node Stimulation in Humans: Reproducibility on 18-Month Follow-up," *Europace*, 2010; 12:1719-1724. Published online on Sep. 27, 2010.
Roy et al., "Rhythm Control Versus Rate Control for Atrial Fibrillation and Heart Failure," *The New England Journal of Medicine*, Jun. 19, 2008; 358(25):2667-2677.
Rutecki, "Anatomical, Physiological, and Theoretical Basis for the Antiepileptic Effect of Vagus Nerve Stimulation," *Epilepsia*, 1990; 31(Suppl. 2):S1-56.
Saksena et al., "Prevention of Atrial Fibrillation by Pacing," Chapter 6 in *Recent Advances in Cardiac Pacing: Goals for the 21st Century*, Barold et al., Eds., 1998, Armonk, NY. Cover page, copyright page and pp. 101-114.
Sato et al., "Age-Related Changes of Cardiac Control Function in Man," *Journal of Gerontology*, 1981; 36(5):564-572.

(56) References Cited

OTHER PUBLICATIONS

Schwartz et al., "Long Term Vagal Stimulation in Patients with Advanced Heart Failure: First Experience in Man," *European Journal of Heart Failure*, 2008; 10:884-891.
Severtson et a., "Vagal Nerve Monitoring: A Comparison of Techniques in a Canine Model," *American Journal of Otology*, 1997; 18(3):398-400.
Sharma et al., "The Importance of Tumor Necrosis Factor and Lipoproteins in the Pathogenesis of Chronic Heart Failure," *Heart Failure Monitor*, 2001; 2(2):42-47.
Shishehbor et al., "Inflammation: Implications for Understanding the Heart-Brain Connection," *Cleveland Clinic Journal of Medicine*, Feb. 2007; 74(Suppl 1): S37-S41.
Subramanian, "Clinical Experience with Minimally Invasive Reoperative Coronary Bypass Surgery," *Eur. J. Cardio-Thorac. Surg.*, 1996, 10:1058-1062. (Abstract Only).
Tan et al., "Cardiac Myocyte Necrosis Induced by Angiotensin II," *Circulation Research*, 1991; 69(5):1185-1195.
Tarver et al., "Clinical Experience with a Helical Bipolar Stimulating Lead," *PACE*, Oct. 1992; 15(10 PartII):1545-1556.
Taylor, "Anticholinesterase Agents," Goodman and Gilman's Pharmacological Basis of Therapeutics, 6th Ed. MacMillian Publishing Co., Inc., New York, 1980; pp. 104-108.
Taylor, "Multiple-electrode Nerve Cuffs for Low-velocity and Velocity-selective Neural Recording," *Med. Biol. Eng. Comput.*, 2004; 42:634-643.
Terry et al., "An Implantable Neurocybernetic Prosthesis System," *Epilepsia*, 1990; 31(Suppl. 2):533-537.
Thompson et al., "Bradycardia Induced by Intravascular Versus Direct Stimulation of the Vagus Nerve," *Ann. Thorac. Surg.*, 1998; 65:637-642.
Tosato et al., "Closed-loop Control of the Heart Rate by Electrical Stimulation of the Vagus Nerve," *Med. Biol. Eng. Comput.*, 2006; 44:161-169.
Tougas et al., "Effects of Chronic Left Vagal Stimulation on Visceral Vagal Function in Man," *PACE*, Oct. 1992; 15(10 PartII):1588-1596.
Tougas et al., "Evidence of Impaired Afferent Vagal Function in Patients with Diabetes Gastroparesis," *PACE*, Oct. 1992; 15(10 PartII):1597-1602.
Tracey, "Physiology and Immunology of the Cholinergic Antiinflammatory Pathway," *The Journal of Clinical Investigation*, Feb. 2007; 117(2):289-296.
Upton, Editorial, *PACE*, Oct. 1992; 15(10 PartII):1543-1544.
Urthaler, "Experimental Studies on Pathogensis of Asystole After Verapamil in the Dog," *Am. J. Cardiol.*, Oct. 1979; 44(4):651-656 (Abstract Only).
Uthman et al., "Efficacy and Safety of Vagus Nerve Stimulation in Patients with Complex Partial Seizure," *Epilepsia*, 1990, 31(Suppl. 2):S44-S50.
Vardas et al., "AAIR Versus DDDR Pacing in Patients with Impaired Sinus Node Chronotropy: An Echocardiographic and Cardiopulmonary Study," *PACE*, Jul. 1997; 20:1762-1768.
Watkins et al., "Implications of Immune-to-Brain Communications for Sickness and Pain," *Proc. Natl. Acad. Sci. USA*, Jul. 1999; 96:7710-7713.
Watkins et al., "Glia: A Novel Drug Discovery Target for Clinical Pain," Nature Reviews Drug Discovery, 2003; 2:973-985.
Westaby, "Coronary Surgery Without Cardiopulmonary Bypass," *British Heart Journal*, 1995; 73:203-205.
Wilder, "Vagus Nerve Stimulation for the Control of Epilepsy," *Epilepsia*, vol. 31, Supplement 2, 1990, pp. S1-S60; Conference Proceedings in conjunction with American Epilepsy Society Annual Meeting, Boston, MA, Dec. 2, 1989. Cover pages, Table of Contents, Foreword, and Summary and Conclusions; 6 pgs. (Each article listed in the Table of Contents is included separately in the Information Disclosure Statement).
Wilkoff et al., "Critical Analysis of Dual-Chamber Implantable Cardioverter-Defibrillator Arrhythmia Detection," *Circulation*, Jan. 23, 2001, 103(3):381-386.
Woodbury et al., "Effects of Vagal Stimulation on Experimentally Induced Seizures in Rats," *Epilepsia*, 1990; 31(Suppl. 2):S7-S19.
Yeh et al., "Geriatric Cachexia: The Role of Cytokines," *Am. J. Clin. Nutr.*, 1999; 70:183-197.
Yokoyama et al., "Cellular Basis for the Negative Inotropic Effects of Tumor Necrosis Factor-α in the Adult Mammalian Heart," *The Journal of Clinical Investigation*, Nov. 1993; 92:2303-2312.
Yokoyama et al., "Tumor Necrosis Factor-α Provokes a Hypertrophic Growth Response in Adult Cardiac Myocytes," *Circulation*, 1997; 95:1247-1252.
Zhang et al., "Optimal Ventricular Rate Slowing During Atrial Fibrillation by Feedback AV Nodal-Selective Vagal Stimulation" *Am. J. Physiol. Heart Circ. Physiol.*, 2002; 282:H1102-H1110.
Zhang et al., "Achieving Regular Slow Rhythm During Atrial Fibrillation Without Atrioventricular Nodal Ablation: Selective Vagal Stimulation Plus Ventricular Pacing" *Heart Rhythm*, 2004; 1(4):469-475.
Zhang et al., "Chronic Atrioventricular Nodal Vagal Stimulation: First Evidence for Long-Term Ventricular Rate Control in Canine Atrial Fibrillation Model," *Circulation*, 2005; 112:2904-2911.
Zhuang et al., "Ventricular Rate Control by Selective Vagal Stimulation is Superior to Rhythm Regularization by Atrioventricular Nodal Ablation and Pacing During Atrial Fibrillation," *Circulation*, 2002; 106:1853-1858.
International Search Report, PCT/US/2008/059723, Aug. 27, 2008, 6 pgs.
Written Opinion, PCT/US/2008/059723, Aug. 27, 2008, 7 pgs.
International Preliminary Report on Patentability, PCT/US/2008/059723, Oct. 27, 2009, 8 pgs.
International Search Report and Written Opinion, PCT/EP2010/003956, dated Nov. 4, 2010, 11 pgs.
Reply to Written Opinion, PCT/EP2010/003956 (WO 2011/000558) dated May 2, 2011, 4 pgs.
International Preliminary Report on Patentability, PCT/EP2010/003956, dated Jul. 20, 2011, 10 pgs.
Office Action for U.S. Appl. No. 11/740,565, mailed Dec. 30, 2009, 8 pages.
Responsive Amendment to Office Action for U.S. Appl. No. 11/740,565, filed Apr. 29, 2010, 11 pages.
Final Office Action for U.S. Appl. No. 11/740,565, mailed Jan. 21, 2011, 9 pages.
Responsive Amendment to Office Action for U.S. Appl. No. 11/740,565, filed Mar. 21, 2011, 8 pages.
Vollman et al., "Automatic 50 Hertz Burst Pacing for the Termination of Atrial Fibrillation: Manual Success Analysis in Patients with Intermittent Atrial Tachyarrhythmias and a Novel Dual-Chamber Implantable Cardioverter Defibrillator," *Circulation*, Oct. 23, 2001;Abstract 1829;104(17):II-384.

* cited by examiner

NERVE SIGNAL DIFFERENTIATION IN CARDIAC THERAPY

CROSS-REFERENCE TO RELATED APPLICATION

The present application is a divisional of patent application Ser. No. 12/848,019 filed on Jul. 30, 2010, (now U.S. Pat. No. 8,639,327), which claims the benefit of U.S. Provisional Patent Application Ser. No. 61/397,702, having a filing date of Apr. 29, 2010, which resulted from conversion of U.S. patent application Ser. No. 12/770,275 filed Apr. 29, 2010 thereto, the disclosures of which are incorporated herein by reference in their entirety. The present application is related to another co-pending and concurrently-filed application, which is hereby incorporated by reference, in its entirety, and which is U.S. patent application Ser. No. 12/770,227 filed Apr. 29, 2010 entitled NERVE SIGNAL DIFFERENTIATION IN CARDIAC THERAPY which was converted to U.S. Provisional Patent Application Ser. No. 61/397,703.

BACKGROUND

The present disclosure relates to nerve signal differentiation; and, more particularly, delivering therapy using such nerve signal differentiation.

Nerve tissue contains both efferent fibers and afferent fibers. Electrical signals propagate from the central nervous system to tissue/organs along efferent fibers while electrical signals propagate from tissues/organs to the central nervous system along afferent fibers. The efferent and afferent fibers play different roles in neuronal regulation (e.g., regulation of the heart).

Further a variety of patient therapies exist that may benefit from nerve recordings. For example, certain therapies may be delivered based on such nerve recordings.

SUMMARY

The disclosure herein relates generally to devices and methods of analyzing nerve signals and/or delivering therapy based on nerve signals. For example, such methods and devices may differentiate between efferent and afferent components of a nerve signal for use with therapy, and further, may initiate or adjust therapy based on the efferent and/or afferent components.

An exemplary device for delivering therapy disclosed herein may include monitoring apparatus, a sensing module, a therapy delivery module, and a control module. The monitoring apparatus is configured to monitor physiological parameters of a patient and includes at least two electrodes configured to monitor electrical activity of the patient's vagus nerve. The sensing module is operably coupled to the monitoring apparatus and configured to receive the monitored physiological parameters. The therapy delivery module is configured to deliver cardiac therapy to to the patient. The control module is operably coupled to the sensing module and to the therapy delivery module. Further, the control module is configured to differentiate between efferent activity and afferent activity of the monitored electrical activity of the patient's vagus nerve, analyze the monitored physiological parameters by at least determining whether the efferent activity of the electrical activity of the patient's vagus nerve is reduced over time, and initiate or adjust cardiac therapy to the patient if the efferent activity of the electrical activity of the patient's vagus nerve is reduced.

In one or more embodiments of the devices disclosed herein, the control module is further configured to determine whether the efferent activity of the electrical activity of the patient's vagus nerve is reduced by at least comparing the pulses per second of the efferent activity to a selected value or by at least comparing the pulses per second of presently-monitored efferent activity to the pulses per second of previously-monitored efferent activity. Further, the control module may be further configured to determine whether the monitored electrical activity of the patient's vagus nerve includes afferent activity and determine whether the efferent activity of the electrical activity of the patient's vagus nerve is reduced by at least comparing the efferent activity to the afferent activity.

Further, in one or more embodiments of the devices disclosed herein, the control module is further configured to determine whether the efferent activity of the electrical activity of the patient's vagus nerve is reduced by comparing the average amplitude of a selected frequency range of the efferent activity to a selected value, by comparing the average amplitude of a selected frequency range of the presently-monitored efferent activity to the average amplitude of the selected frequency range of previously-monitored efferent activity, by comparing the average power of a selected frequency range of the efferent activity to a selected value, or by comparing the average power of a selected frequency range of the presently-monitored efferent activity to the average power of the selected frequency range of previously-monitored efferent activity. Further, the cardiac therapy may include electrical stimulation to the patient's vagus nerve, and the control module may be further configured to deliver electrical stimulation to the patient's vagus nerve after a burst of efferent activity of the electrical activity of the patient's vagus nerve ceases.

Still further, in one or more embodiments of the devices disclosed herein, the physiological parameters further include electrical activity of the patient's heart and wherein the control module may be further configured to provide a function relating the status of the patient's vagus nerve to the electrical activity of the patient's heart for use in therapy, assess a status of the patient's vagus nerve using the monitored electrical activity of the patient's heart using the function, and initiate or adjust cardiac therapy to the patient based on the assessed status of the patient's vagus nerve.

An exemplary method of delivering therapy disclosed herein may include monitoring physiological parameters of a patient (i.e., where the physiological parameters include electrical activity of at least one nerve fiber of a patient) and determining whether the monitored electrical activity of the patient's vagus nerve includes efferent activity. The exemplary method further includes analyzing the monitored physiological parameters (e.g., analyzing the monitored physiological parameters may include determining whether the efferent activity of the electrical activity of the patient's vagus nerve is reduced over time) and initiating or adjusting cardiac therapy if the efferent activity of the electrical activity of the patient's vagus nerve is reduced.

In one or more embodiments of methods described herein, determining whether the efferent activity of the electrical activity of the patient's vagus nerve is reduced may include comparing the pulses per second of the efferent activity to a selected value, comparing the pulses per second of presently-monitored efferent activity to the pulses per second of previously-monitored efferent activity.

Further, in one or more embodiments of methods described herein, exemplary methods further include determining whether the monitored electrical activity of the patient's vagus nerve includes afferent activity. Thus, determining whether the efferent activity of the electrical activity of the patient's vagus nerve is reduced may include comparing the efferent activity to the afferent activity.

Still further, in one or more embodiments of methods described herein, determining whether the efferent activity of the electrical activity of the patient's vagus nerve is reduced may include comparing the average amplitude of a selected frequency range of the efferent activity to a selected value, comparing the average amplitude of a selected frequency range of the presently-monitored efferent activity to the average amplitude of the selected frequency range of previously-monitored efferent activity, comparing the average power of a selected frequency range of the efferent activity to a selected value, and comparing the average power of a selected frequency range of the presently-monitored efferent activity to the average power of the selected frequency range of previously-monitored efferent activity.

Yet still further, in one or more embodiments of methods described herein, delivering cardiac therapy may include delivering electrical stimulation to the patient's vagus nerve, and the exemplary methods may further include delivering the electrical stimulation to the patient's vagus nerve for a selected period of time after a burst of efferent activity of the electrical activity of the patient's vagus nerve ceases. Further, the physiological parameters may further include electrical activity of the patient's heart, and the exemplary methods may further include: providing a function relating the status of the patient's vagus nerve to the electrical activity of the patient's heart for use in therapy, assessing a status of the patient's vagus nerve using the monitored electrical activity of the patient's heart using the function, and initiating or adjusting cardiac therapy to the patient based on the assessed status of the patient's vagus nerve.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
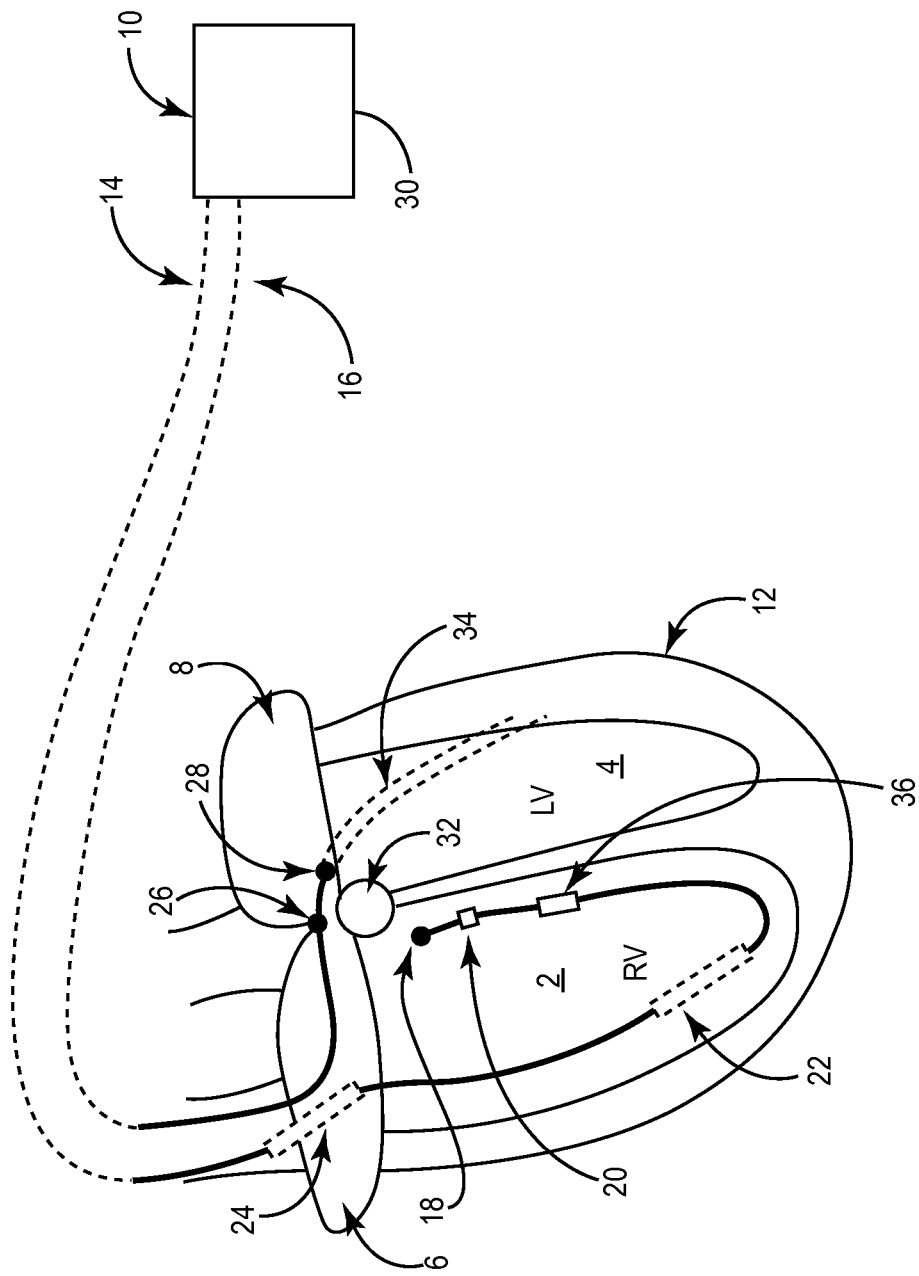
FIG. 1 is a schematic diagram of an implantable medical device (IMD) operably coupled to a patient's heart.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, devices, and systems are described with reference to FIGS. 1-10. Elements or processes from one embodiment can be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the process operations and/or the size and shape of various elements herein may be modified but still fall within the scope of the present disclosure, although certain timing, one or more shapes and/or sizes, or types of elements, may be advantageous over others.

Figure 2:
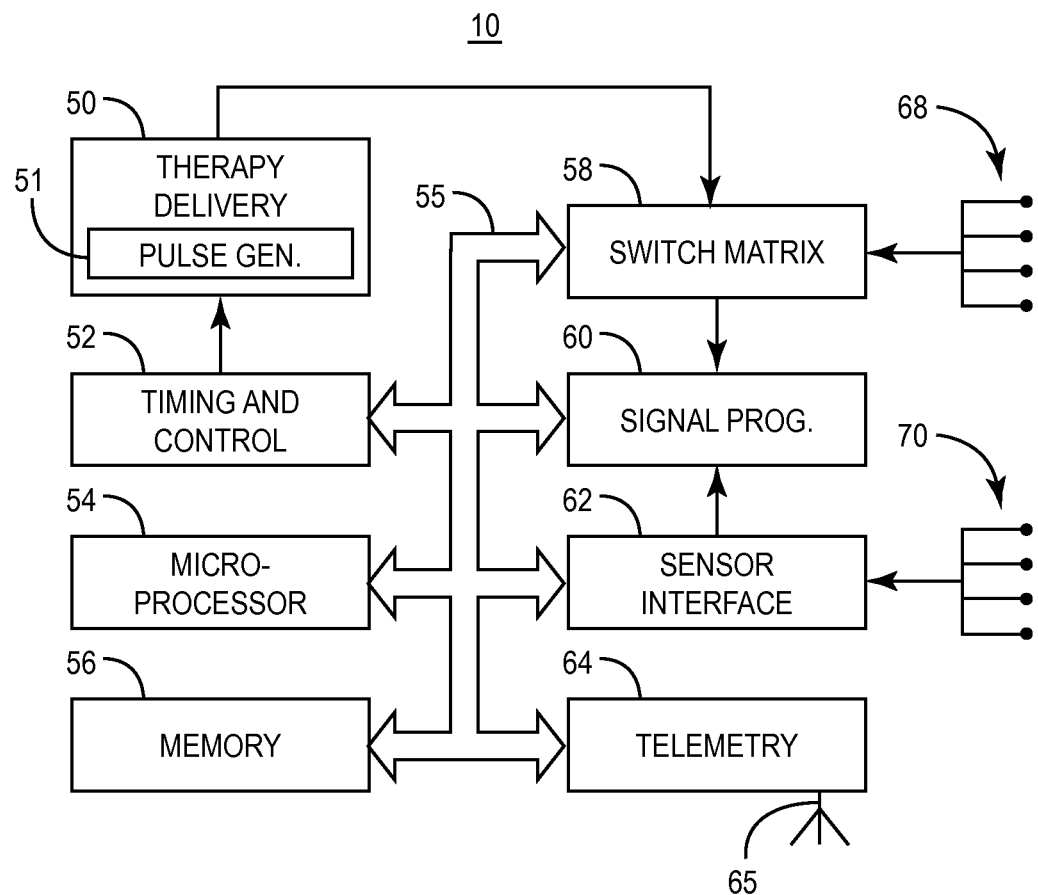
FIG. 2 is a block diagram of the IMD shown in FIG. 9.

Referring to FIGS. 1-2, IMD 10 is configured to monitor physiological parameters of the patient (e.g., the efferent and/or afferent of the electrical activity of the patient's nerves, the parasympathetic and/or parasympathetic signals of the patient's nerves) and to deliver therapy using two leads. Although the IMD 10 depicted in FIG. 1 uses two leads, a single lead or more than two leads may be used with the methods, devices, and systems described herein. For example, the IMD 10 may use one lead that includes a single electrode positionable near the atrioventricular node in the base of the right ventricle. The single electrode may be used for both either atrial or ventricular pacing/sensing and vagal recording/stimulation. Further, for example, the IMD 10 may use a first lead including an electrode for placement proximate a nerve a patient and a second lead including an electrode for placement proximate the same nerve of the patient but closer to the peripheral end of the nerve than the electrode of the first lead (e.g., for use in recording nerve signals and differentiating between efferent and afferent components of the nerve signals).

As shown, the IMD 10 is coupled to two transvenous leads: a right ventricular (RV) lead 14 and a coronary sinus (CS) lead 16. RV lead 14 includes a distal tip electrode 18 deployed in the basal region of the right ventricle 2 in operative relation to the AV node 32. Ring electrode 20 is spaced proximally from tip electrode 18 for use in bipolar sensing and pacing in the right ventricle 2. According to one embodiment, tip electrode 18 may be used in conjunction with IMD housing 30 (for unipolar sense/stimulation) or ring electrode 20 (for bipolar sense/stimulation) for sensing ventricular signals, for detecting a ventricular rhythm, for delivering cardiac pacing pulses in the right ventricle, for monitoring the ST segment, for recording/monitoring the electrical activity of the vagus nerve, and for delivering vagal stimulation pulses in the right ventricle (e.g., for discriminating SVT and VT). RV lead 14 may further include coil electrodes 22 and 24 for use in delivering high-energy shock pulses for cardioversion and defibrillation therapies. Other embodiments may include additional electrodes adapted for sensing and stimulating the right atrium 6, either on a separate right atrial lead or included along RV lead 14, recording the electrical activity of various nerves (e.g., the vagus nerve), etc. Further, such electrodes may be positioned relative to the SA node and or AV node for vagal stimulation or for recording/monitoring of the electrical activity of the vagus nerve (e.g., portions of the vagus nerve located in the heart 12).

RV lead 14 further includes sensor 36 used for sensing signals other than cardiac electrical signals, such as mechanical signals, e.g., accelerometer sensing, hemodynamic pressure, flow, myocardial acceleration, heart sound, tissue perfusion, lung fluid status, etc., or blood chemistry signals, e.g., temperature, oxygen saturation, pH, etc. In one embodiment, sensor 36 is embodied as a pressure sensor (e.g., for monitoring various blood pressures and pressure drops) to, e.g., be used in verifying effective vagal stimulation. Further, for example, sensor 36 may be an oxygen sensor, as disclosed in U.S. Pat. No. 4,750,495 issued to Moore et al. on Jul. 31, 1989, a pressure transducer as disclosed in U.S. Pat. No. 4,485,813 issued to Anderson et al. on Dec. 4, 1984, a physical activity sensor as disclosed in U.S. Pat. No. 4,428,378, issued to Anderson et al on Jan. 31, 1984, or a ventricular impedance plethysmograph as disclosed in U.S. Pat. No. 4,535,774 issued to Olson on Aug. 20, 1985, all of which are incorporated herein by reference in their entireties.

Coronary sinus lead 16 is deployed in a cardiac vein 34 via the coronary sinus for positioning electrodes 26 and 28 in operative relation to the left chambers of heart 12. In particular, in one embodiment, electrodes 26 and 28 are positioned near the AV node 32 to, e.g., allow electrical stimulation of the vagus nerve for discrimination of SVT and VT, for blocking conduction of the AV node 32, etc. Further, electrode 26 may be positioned proximate the coronary sinus. Electrodes 26 and 28 may also be used for sensing cardiac signals and for delivering cardiac pacing pulses in the left ventricle 4. It is recognized that coronary sinus lead 16 may carry additional electrodes such as a coil electrode for use in delivering high energy shock pulses, additional ring electrodes, and/or a tip electrode for cardiac sensing and pacing in the left atrium 8.

Furthermore, the embodiments described herein are not limited for use with transvenous leads as shown in FIG. 1. For example, other embodiments may include the use of epicardial electrodes positioned in operative relation to the fatty pad near the SA node and/or the fatty pad near the AV node. Further, subcutaneous electrodes may be incorporated on the housing 30 of IMD 10 and/or positioned on subcutaneous leads extending from IMD 10 for use in sensing cardiac signals and delivering electrical stimulation pulses, e.g., for delivering cardiac pacing and shock therapies. Numerous alternative electrode configurations may be appropriate for nerve recordings and vagal stimulation, including endocardial or epicardial electrodes deployed near or adjacent the SA nodal and/or AV nodal fatty pads or electrodes positioned along the vagus nerve branches.

FIG. 2 is a functional block diagram of IMD 10 shown in FIG. 1. Although the IMD 10 has previously been described with respect to a patient's heart, IMD 10 may used for monitoring and delivering therapy to any organs or parts of a patient. IMD 10 generally includes timing and control circuitry 52 and an operating system that may employ microprocessor 54 or a digital state machine for timing sensing and therapy delivery functions and controlling other device functions in accordance with a programmed operating mode. Microprocessor 54 and associated memory 56 (e.g. read only memory, random access memory, etc.) are coupled to the various components of IMD 10 via a data/address bus 55. IMD 10 includes therapy delivery module 50 for delivering a therapy, such as an electrical stimulation or drug therapy, under the control of timing and control circuitry 52. Therapy delivery module 50 includes pulse-generating circuitry 51 for generating electrical stimulation pulses (e.g., bursts of electrical stimulation pulses) under the control of timing and control circuitry 52. As will be described herein, pulse-generating circuitry 51 generates stimulation pulses for stimulating the vagus nerve.

For delivering electrical stimulation pulses, pulse-generating circuitry 51 may be coupled to two or more electrodes 68 via a switch matrix 58. Switch matrix 58 is used for selecting which electrodes and corresponding polarities are used for delivering electrical stimulation pulses. Electrodes 68 may include lead-based electrodes, leadless electrodes incorporated on IMD 10, and/or the IMD housing configured for use as a can or case electrode. Therapy delivery module 50 may further include high voltage circuitry for generating high voltage cardioversion/defibrillation shocks. Aspects of the present disclosure may be embodied in an implantable cardioverter defibrillator including high voltage circuitry as generally disclosed in U.S. Pat. No. 6,731,978 to Olson et al., incorporated herein by reference in its entirety.

Electrodes 68 may also be used for sensing electrical signals within the body, such as cardiac signals and/or nerve signals. Cardiac electrical signals are sensed using any of electrodes 68 for detecting the heart rhythm and determining when and what therapy is needed, and in controlling the timing of stimulation pulses. In other words, the IMD 10 includes monitoring apparatus, which includes electrodes 68 amongst other things. As will be described herein, cardiac electrical signals may be sensed following delivery of vagal stimulation for adjusting the vagal stimulation, for verifying the effectiveness of the vagal stimulation, and/or for detecting, and/or discriminating between cardiac conditions (e.g., SVT, VTNF, etc.). Nerve signals are sensed using any of the electrodes 68 for detecting the electrical activity (e.g., parasympathetic activity, etc.) of various nerves.

Electrodes used for sensing and electrodes used for stimulation may be selected via switch matrix 58. When used for sensing, electrodes 68 are coupled to signal processing circuitry 60 via switch matrix 58. Processing circuitry 60 includes sense amplifiers and may include other signal conditioning circuitry and an analog to digital converter. In other words, the IMD 10 may include a sensing module, e.g., includes switch matrix 58, signal processing circuitry 60, etc. Electrically sensed signals may then be used by microprocessor 54 for detecting physiological events, such as detecting and discriminating cardiac arrhythmias. Further, the microprocessor 54 may have the ability to program amplifiers and other electronic circuits for monitoring neuronal signals (to, e.g., adjust the magnitude of the gain, the filtering, the sampling rate, etc.) and to processes raw data for integration, data analysis, and comparison of signals.

The monitoring apparatus of the IMD 10 may further include sensors 70 such as pressure sensors, accelerometers, flow sensors, blood chemistry sensors, activity sensors, and/or other physiological sensors known for use with IMDs. Sensors 70 are coupled to IMD 10 via a sensor interface 62 which provides sensor signals to signal processing circuitry 60. Sensor signals are used by microprocessor 54 for detecting physiological events or conditions. For example, IMD 10 may monitor heart wall motion, blood pressure, blood chemistry, respiration, and/or patient activity. Monitored signals may be used for sensing the need for delivering, adjusting, terminating, and/or initiating therapy under control of the operating system. In other words, the IMD 10 may include a control module, which may include the microprocessor 54 and memory 56 and may be configured using an operating system.

The operating system includes associated memory 56 for storing a variety of programmed-in operating mode and parameter values that are used by microprocessor 54. The memory 56 may also be used for storing data compiled from sensed signals and/or relating to device operating history (e.g., nerve recording information, for use in differentiating between efferent and afferent components of a nerve recording, for use in delivering, adjusting, controlling, initiating, and/or terminating therapy) and/or for communicating such data outside of the patient (e.g., using telemetry communication out of recorded history on receipt of a retrieval or interrogation instruction).

IMD 10 further includes telemetry circuitry 64 and antenna 65. Programming commands or data are transmitted during uplink or downlink telemetry between IMD telemetry circuitry 64 and external telemetry circuitry included in a programmer or home monitoring unit.

As described, IMD 10 is able to monitor and analyze electrical activity of a patient's nerve tissue. Nerve tissue (e.g., peripheral nerves or central nerve projections) contain both efferent fibers and afferent fibers. Electrical signals propagate from the central nervous system to tissue/organs along efferent fibers while electrical signals propagate from tissues/organs to the central nervous system along afferent fibers. The efferent and afferent fibers play different roles in neuronal regulation (e.g., regulation of the heart). The disclosure herein describes techniques and systems/devices to differentiate efferent components from afferent components in nerve recordings. For example, the efferent and afferent components (e.g., the action potential propagation directions) can be differentiated by analyzing the neuronal waveforms and propagation direction.

Further, the efficacy and efficiency of certain therapies may be improved using the differentiation of efferent and afferent components in nerve recordings. In at least one embodiment, assessment of vagal (parasympathetic) efferent activities in nerve recordings may be useful during neuromodulation.

The methods described herein may be implemented by various devices (e.g., implantable medical devices) and systems. For example, therapy systems such as therapy system 10, shown and described in provisional application 61/299,816 filed on Jan. 29, 2010 and entitled THERAPY SYSTEM INCLUDING CARDIAC RHYTHM THERAPY AND NEUROSTIMULATION CAPABILITIES, is capable of implementing teachings of the present disclosure. Such devices and systems may include one or more leads, electronic circuits, power sources, sensors, electrodes, fluid delivery devices, etc. Further, such devices and systems may be configured to monitor one or more physiological parameters of a patient, e.g., electrical activity of a patient's heart, chemical activity of a patient's heart, chemical activity or pressure levels of a patient's gastrointestinal (GI) system, hemodynamic activity of a patient's heart, electrical activity of a patient's muscles, and electrical activity of a patient's nerves (e.g., vagus nerve, splanchnic nerves, etc.).

The electrical activity of a patient's heart may include one or more signals that may be monitored (e.g., using electrodes) from locations in or around the patient's heart. Using such monitored electrical activity of a patient's heart, certain metrics may be determined and collected (e.g., for analysis). For instance, the following metrics may be determined and collected using the electrical activity of the patient's heart: heart rate (HR), heart rate variability (HRV), heart rate turbulence (HRT), deceleration/acceleration capacity, T-wave alternans (TWA), electrocardiogram, P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment, T-wave changes, QT intervals, electrical vectors, etc.

The chemical activity of a patient's heart may include one or more chemical properties that may be monitored (e.g., using various sensors) from locations in or around the patient's heart. Using such monitored chemical activity of a patient's heart, certain metrics may be determined and collected (e.g., for analysis). For instance, the following metrics may be determined and collected using the chemical activity of the patient's heart: oxygen saturation, brain natriuretic peptide (BNP) (proteins/peptides) content, pH, lung fluid status, catecholamines, blood electrolytes (K+, Ca++, Na+, etc.), etc.

The hemodynamic pressure of a patient's heart may include one or more hemodynamic pressures that may be monitored (e.g., using various sensors) from locations in or around the patient's heart. Using such monitored hemodynamic pressures of a patient's heart, certain metrics may be determined and collected (e.g., for analysis). For instance, the following metrics may be determined and collected using the hemodynamic pressures of the patient's heart (e.g., using Medtronic OptiVol Fluid Status Monitoring): mean arterial pressure, diastolic blood pressure, systolic blood pressure, flow rates, pressure drops, heart sounds, lung sounds, tissue perfusion, intracardiac pressure, pulmonary vein pressure, cardiac imaging, etc.

The electrical activity of the patient's nerves may include one or more signals and may be monitored (e.g., using electrodes) from locations in or around one or more of the patient's nerves. Such signals may include parasympathetic and/or sympathetic signals propagating along efferent and afferent nerve fibers. In one embodiment, the electrical signals propagating along one or more nerve fibers of the patient's vagus nerve may be monitored. Further, using the methods and systems/devices described herein, the efferent and afferent components of the nerve signals may be differentiated such that, e.g. the efferent and the afferent components may be identified, monitored, and analyzed.

Figure 3:
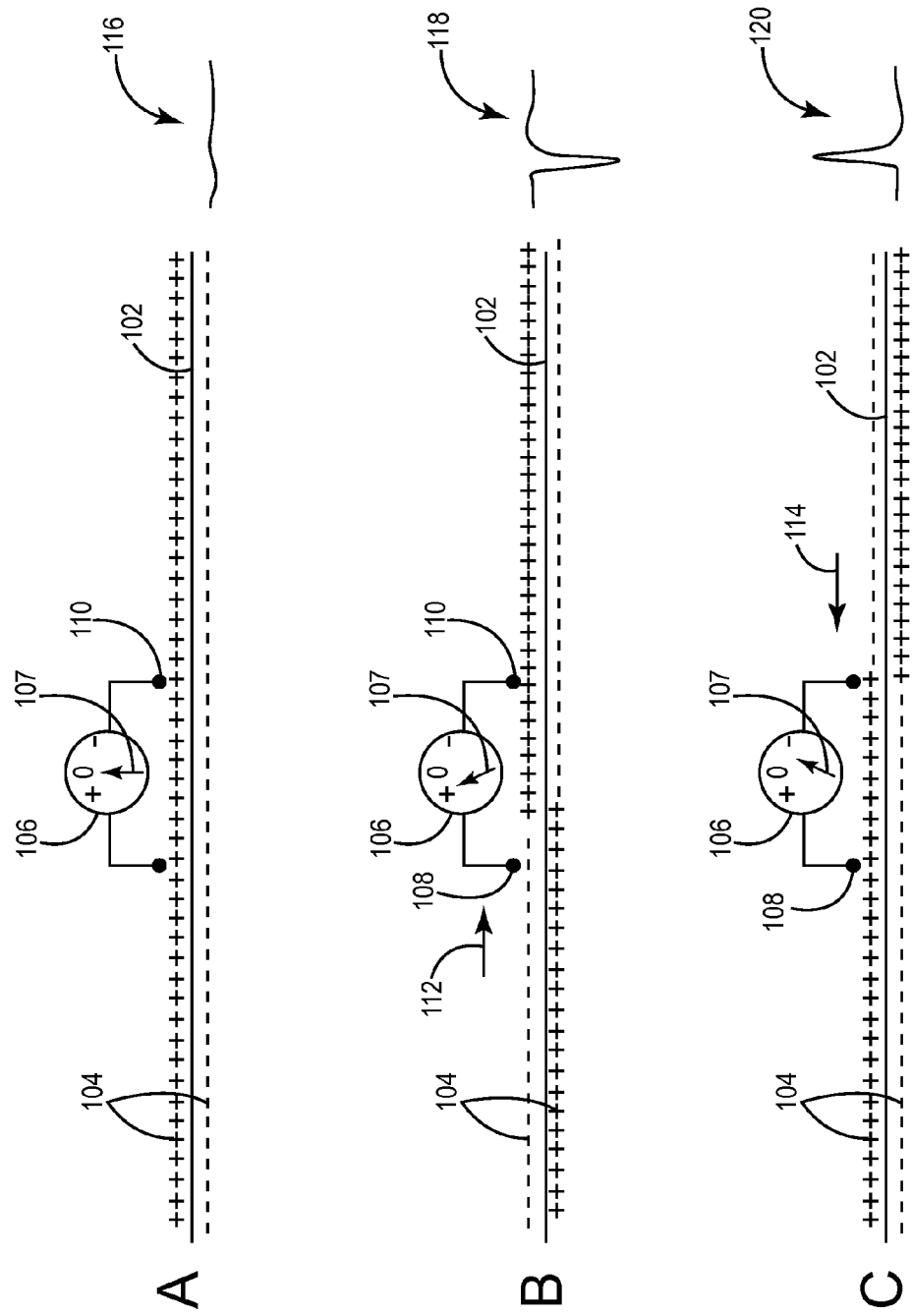
FIG. 3 is a diagram of nerve signals propagating across a pair of electrodes.

Three diagrams of nerve signals propagating across a pair of electrodes are depicted in FIG. 3. Each of diagrams A, B, and C of FIG. 3 includes solid lines representative of the cell membrane of nerve fibers 102 and plus/minus symbols representative the cell membrane potential and its action potential propagation 104 along the respective nerve fibers 102. Further, each of diagrams A, B, and C includes a first electrode 108, a second electrode 110, and a sensing module 106 configured to monitor the electrical signals captured by the first electrode 108 and the second electrode 110. Referring briefly to FIG. 1, first electrode 108 is tip electrode 18 and a second electrode 110 can be ring electrode 20 on a single lead. The first electrode 108 and second electrode 110 may be located along the nerve fibers 102 such that the first electrode 108 is closer to a central end (i.e., corresponding to the direction towards the central nervous system of a patient) of the nerve fibers 102 than the second electrode 110 and the second electrode 110 is closer to a peripheral end (i.e., corresponding to the direction towards the tissue and/or organs of a patient) of the nerve fibers 102 than the first electrode 108. In other words, the second electrode 110 may be located further along the nerve fibers 102 than the first electrode 108.

Further, the first electrode 108 may be described herein as being located a selected distance away from the second electrode 110 such that the first electrode 108 and the second electrode 110 are spaced along the nerve fibers 102 as described herein (i.e., the first electrode 108 is located closer to the central end than the second electrode 110). The selected distance may be about 1 millimeter (mm) to about 10 mm. If the electrodes are located too close to one another, the amplitude of the signals may be too small. Further, if the electrodes are located too far from one another, then the signals may be similar to a biphasic waveform with a positive portion and a negative portion spaced apart from one another.

Diagram A of FIG. 3 depicts an action potential of the nerve fibers 102 at rest. In other words, no electrical signals are propagating along the nerve fibers 102. As a result, the sensing module 106 is not detecting either a positive or negative waveform (e.g., using the first electrode or the second electrode as shown by no voltage change between the first or second electrode 108, 110) as shown by the arrow indicator 107 within the sensing module 106 and the voltage versus time graph 116.

Diagram B of FIG. 1 depicts an action potential of the nerve fibers moving from the central end to the peripheral end as shown by arrow 112. In other words, electrical signals are propagating along the nerve fibers 102 from the central end to the peripheral end. As a result, the sensing module 106 is detecting a negative waveform (e.g., using the first electrode 108 and the second electrode 110 as shown by a voltage shift between the first and second electrode 108, 110 with the first electrode 108 detecting the membrane potential change first) as shown by the arrow indicator 107 within the sensing module 106 and the voltage versus time graph 118.

Diagram C of FIG. 1 depicts an action potential of the nerve fibers moving from the peripheral end to the central end as shown by arrow 114. In other words, electrical signals are propagating along the nerve fibers 102 from the peripheral end to the central end. As a result, the sensing module 106 is detecting a positive waveform (e.g., using the first electrode 108 and the second electrode 110 as shown by a voltage shift between the first and second electrode 108, 110 with the second electrode 110 detecting the membrane potential change first) as shown by the arrow indicator 107 within the sensing module 106 and the voltage versus time graph 120.

Figure 4A:
FIGS. 4A-4B depict two exemplary leads, respectively, that may include the electrodes shown in FIG. 3.
Figure 4B:
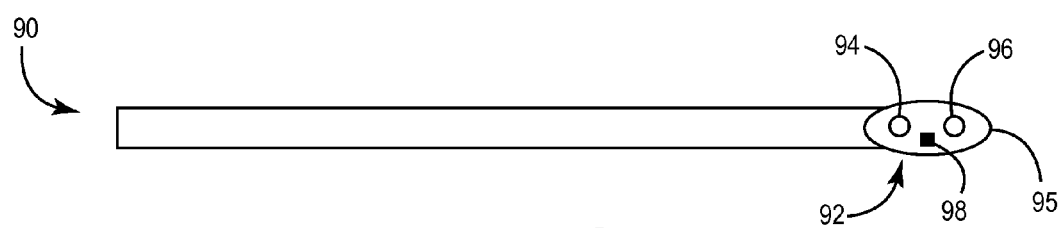

Various leads may be used for recording/monitoring the electrical activity of one or more nerve tissues (e.g., stimulation leads, recording leads, therapy leads, etc.). Further, the process described herein may use one lead having two electrodes or two or more leads each having at least one electrode. Still further, the leads may have purposes other than nerve recording (e.g., muscle stimulation). Two exemplary leads 80, 90 that may be used with the concepts depicted in and described with reference to FIG. 3, as well as the methods described herein, are depicted in FIGS. 4A and 4B, respectively. The distal tip 82 of lead 80 (referred to as an intravascular pacing/recording lead) includes a screw-in electrode 84 (also referred to as a tip electrode) and a ring electrode 86. Such electrodes 84, 86 may be used for various nerve recordings and intravascular pacing/recording (e.g., be located proximate the fatty pad on the atrial epicardium).

The distal tip 92 of the lead 90 (referred to as a minimally invasive nerve recording patch lead) includes a first electrode 94, a second electrode 96, and a suturing hole 98. The distal tip 92 may further include silicon insulation 95 surrounding the electrodes 94, 96 and forming the suturing hole 98. In at least one embodiment, the lead 90, through minimally invasive surgery, may be sutured (e.g., using the suturing hole 98) such that the electrodes 94, 96 are located over a target location, e.g., a fatty pad or nerve bundle.

The electrodes of each lead 80, 90 may be configured such that when the lead is located proximate nerve tissue, each electrode is located along the nerve tissue such that one electrode is located closer to a central end (i.e., corresponding to the central nervous system of a patient) and the other electrode is located closer to the peripheral end (i.e., corresponding to tissue and/or organs of a patient) of the nerve tissue Further, the leads 80, 90 may be used in conjunction with each other. For example, the leads 80, 90 can both be positioned proximate a nerve tissues such that an electrode of lead 80 is located closer to the central end of the nerve fiber than the electrode of lead 90 (such that the leads 80, 90 may be used for nerve signal differentiation as described herein).

If the direction of lead placement cannot be determined at the time of implant (e.g., if the orientation of each electrode with respect to each cannot be determined such as which electrode is closer to the central end of the nerve fiber), then the signals recorded (e.g., electrical activity) on the electrodes may be correlated to certain physiological activities to determine the direction of lead placement. For example, if the lead is located proximate the vagus nerve and the electrical activity recorded on the electrodes is correlated to the slowing of the patient's heart rate, then the electrical activity may be assigned as efferent vagal activity and the electrode that first recorded the electrical activity may be assigned as being closer to the central end.

Figure 5:
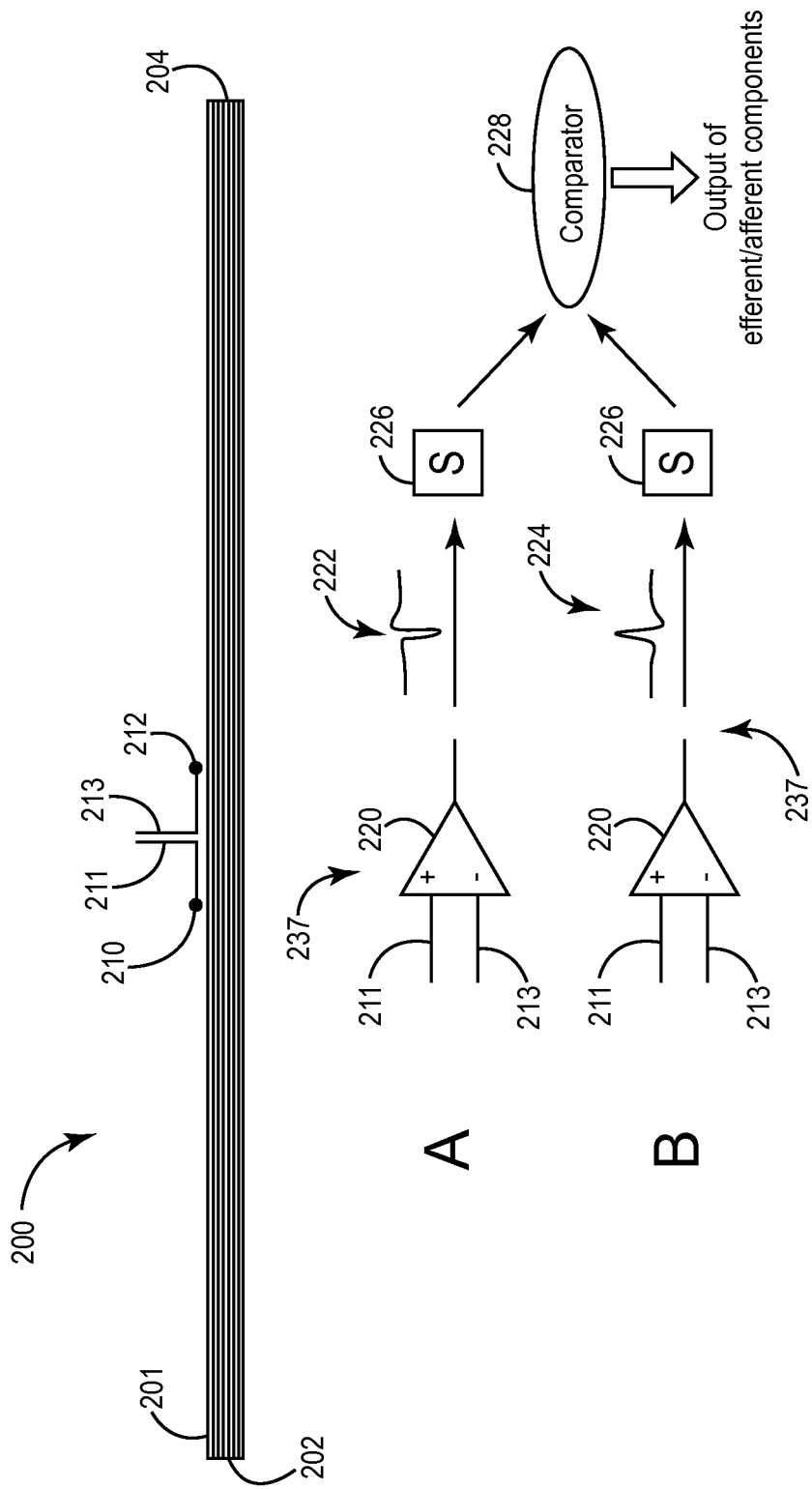
FIG. 5 is a diagram illustrating an exemplary method of nerve signal differentiation using a bipolar electrode configuration.

Some practical applications of the concepts depicted in and described with reference to FIG. 1 are described more specifically with reference to FIGS. 5-6. For example, an exemplary method 200 of nerve signal differentiation using a bipolar electrode configuration (e.g., using two electrodes connected to single amplifier) is depicted in FIG. 5. As depicted, the nerve fibers 201 extend from a central end 202 (i.e., corresponding to the nerve fibers projecting to the central nervous system of a patient) to a peripheral end 204 (i.e., corresponding to the nerve fibers projecting to tissue and/or organs of the patient). Such nerve fibers 201 may be part of any one or more portions or branches of a patient's nervous system such as, e.g., the brain, the cerebellum, the spinal cord, the intercostal nerves, the subcostal nerves, the lumbar plexus, the sacral plexus, the femoral nerves, the pudendal nerves, the sciatic nerves, the muscular branches of the femoral nerve, the saphenous nerve, the tibial nerve, the superficial peroneal nerve, the deep peroneal nerve, the common peroneal nerve, the ulnar nerve, the obturator nerve, the genitofemoral nerve, the iliohypogastric nerve, the median nerve, the radial nerve, the musculocutaneous nerve, the brachial plexus, the splanchnic nerves, etc.

In at least one embodiment, the nerve fibers 201 are part of the patient's vagus nerve. Parts of the patient's vagus nerve may be monitored (e.g., the same parts that may be used for vagal stimulation) proximate the sinoatrial (SA) nodal fatty pad, the atrioventricular (AV) nodal fatty pad and along the great vein, and coronary artery, the cervical vagus nerve (e.g., the right or left side), the fat pad located between the medial superior vena cava and aortic root (SVC-Ao fat pad), the fat pad superior to the right pulmonary artery, the fat pad at the IVC-left atrial junction (IVC-LA fat pad), the fat pad proximate the right pulmonary vein-atrial junction (RPV fat pad), the spinal cord (e.g., vertebral levels T1-T12, C1-C8, etc. such as described in U.S. Pat. App. Pub. No. 2002/0107552 A1 to Hill et al., which is incorporated herein by reference in its entirety), and additional intracardiac locations near the SA node, AV node, coronary sinus, and base of right ventricle.

The method 200 includes locating a first electrode 210 and a second electrode 212 along the nerve fibers 201 of a patient to capture the electrical activity propagating along the nerve fibers 201. The first electrode 210 is located closer to the central end 202 of the nerve fibers 201 than the second electrode 212. Conversely, the second electrode 212 is located closer to the peripheral end 204 of the nerve fibers 201 than the first electrode 210. Further, for example, the first electrode 210 may be located about 1 mm to about 10 mm from the second electrode 212. The first electrode 210 and the second electrode 212 may be located on the same lead or on different leads and operably coupled (e.g., electrically coupled) to an IMD or components thereof.

The first electrode 210 and second electrode 212 may be operably coupled (e.g., electrically coupled) to differentiation circuitry 237 for use in differentiating efferent and afferent activity. For example, as shown, the differentiation circuitry 237 includes at least an amplifier 220 (e.g., a component of an IMD) that is operably coupled to the first electrode 210 and the second electrode 212 via connections 211, 213, respectively (i.e., the first electrode 210 is operably coupled to the positive terminal of the amplifier 220 and the second electrode 212 is operably coupled to the negative terminal of the amplifier 220). Further, connections 211, 213, as well as any electrical coupling or connection described herein, may be wired or wireless (e.g., using radio-frequency or optical transmission). When an electrical signal propagates from the central end 202 to the peripheral end 204 of the nerve fibers 201, the amplifier 220 outputs a negative waveform 222 as shown in Diagram A thereby indicating that the electrical signal has an efferent component. When an electrical signal propagates from the peripheral end 204 to the central end 202 of the nerve fibers 201, the amplifier 220 outputs a positive waveform 224 as shown in Diagram B thereby indicating that the electrical signal has an afferent component. Further, if the first electrode 210 and the second electrode 212 were coupled to the differentiation circuitry 237 oppositely (e.g., the first electrode 210 was operably coupled to the negative terminal of the amplifier 220 and the second electrode 212 was operably coupled to the positive terminal of the amplifier 220), an efferent component would be indicated by a positive waveform while an afferent component would be indicated by a negative waveform. Furthermore, the amplifier 220 may possess a programmable gain and/or filtering features for optimal processing of nerve signals, and further for auto-adjusting the crossing threshold for collecting efferent or afferent signals. Moreover, electronic components (not shown) may be used in conjunction with the amplifier 220 to provide maximum or minimum derivatives of the nerve signal (e.g., the voltage of the signal) that relate to a fast change between the first and the second waveform of the nerve signals. Such derivatives may be used for integration and summary of the signals collected in a defined time window as described herein.

To determine whether the electrical signal includes efferent or afferent components, method 200 may integrate 226 the electrical signal (e.g., compute the area under the curve) to generate a signal value. The signal value may be compared 228 to one or more selected threshold values to determine whether the electric signal includes efferent or afferent activity (e.g., as opposed to background/baseline signals and/or noise). The threshold values may be about two to about three times a baseline value (e.g., the baseline value of electrical activity measured on the nerve fibers 201). If the signal value is greater than the efferent threshold value, then the electrical activity is determined to contain efferent components. Efferent activity, in this configuration, generates a negative polarity, and therefore, the efferent threshold value may be a negative value or the absolute value of the electrical activity may be used in the comparison. If the efferent threshold value is a negative value, then instead of determining if the signal value is greater than the efferent threshold value, the method may determine if the signal value is less than the efferent threshold value. If the absolute value of the electrical activity is used in the comparison, then the method would determine if the signal value is greater than the efferent threshold value and whether the electrical activity has a negative polarity to determine that the electrical activity is efferent.

If the signal value is greater than the afferent threshold value, then the electrical activity is determined to contain afferent components. Afferent activity, in this configuration, generates a positive polarity, and therefore, the threshold value may be a positive value. As such, the method may determine if the signal value is greater than the afferent threshold value to determine if the electrical activity includes afferent activity. Such determinations of afferent or efferent activity may be reversed depending on the location of the electrodes, e.g., if the second electrode is located closer to the central end. Further, such differentiations between or determinations of efferent/afferent components may used, e.g., in delivering and/or adjusting therapy to a patient.

To recap, the method 200 may determine whether the electrical signals propagating along the nerve fibers 201 include efferent or afferent components. As such, a nerve signal (e.g., two recordings of the same nerve signal recorded at different locations along the nerve fibers 201) may be inputted and a determination whether the electrical signals are efferent and/or afferent may be outputted.

In other words, the first electrode 210 and the second electrode 212 are operably coupled to differentiation circuitry 237 (e.g., a portion of an IMD, and which may include an amplifier 220) that is configured to receive the electrical signals monitored by the first and the second electrodes 210, 212. Further, the differentiation circuitry 237 may include circuitry that is configured to determine whether an electrical signal propagating along the nerve fibers 201 monitored using the first and second electrodes 210, 212 includes efferent activity (and/or afferent activity). In one or more embodiments, certain modules of an IMD may include the functionality of the differentiation circuitry 237. For example, a control module of an IMD may be configured to compare the electrical activity monitored by the first electrode to the electrical activity monitored by the second electrode and determine that the electrical signal includes efferent activity if the comparison between the electrical activity monitored by the first electrode to the electrical activity monitored by the second electrode generates a waveform having a particular polarity (e.g., positive or negative depending on the electrode configuration).

Figure 6:
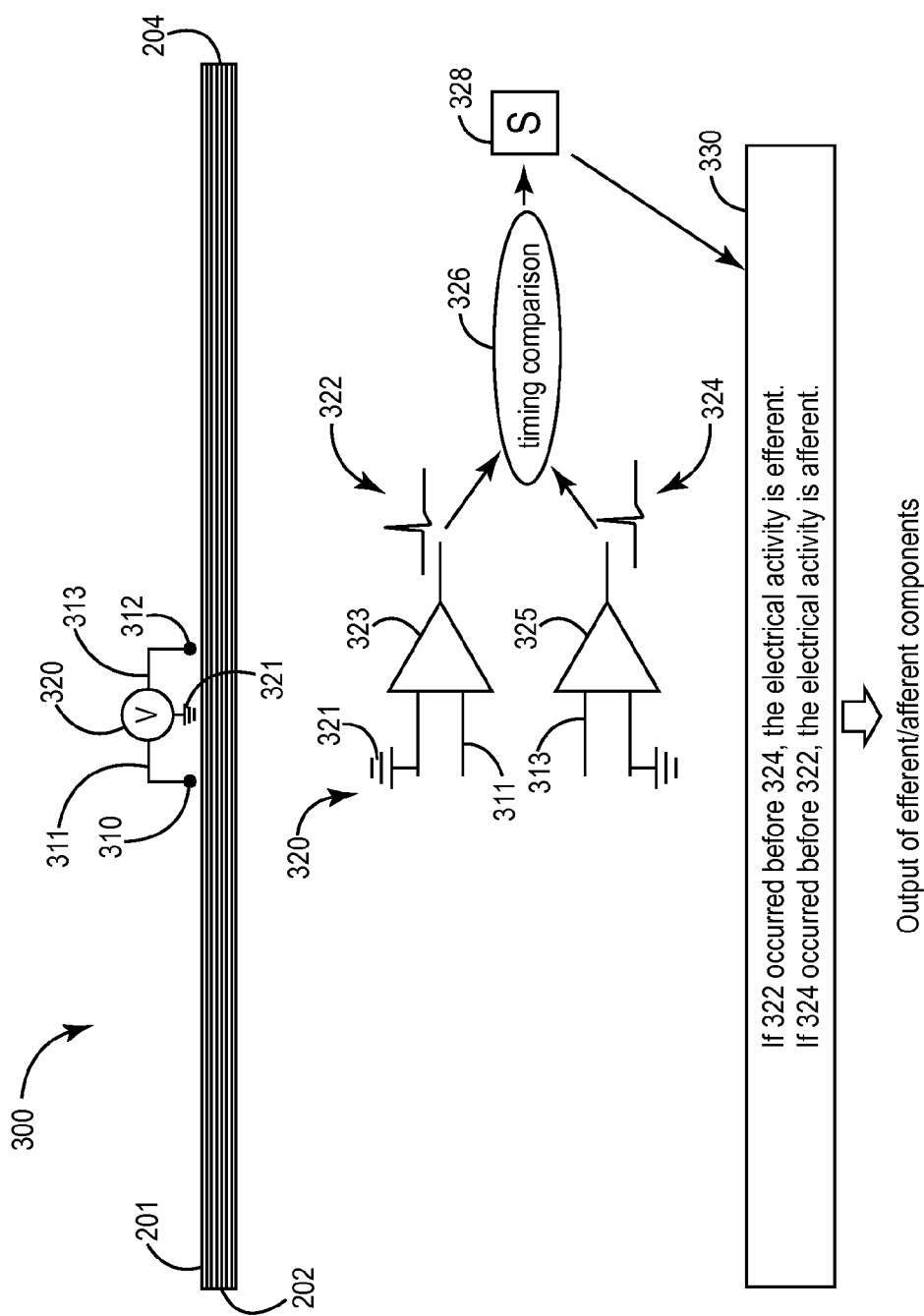
FIG. 6 is a diagram illustrating an exemplary method of nerve signal differentiation using a unipolar electrode configuration.

An exemplary method 300 of nerve signal differentiation using a unipolar electrode configuration is depicted in FIG. 6. The method 300 may be used by itself, or in conjunction with method 200 depicted in FIG. 5 to, e.g., detect neuronal activation when efferent and afferent components occur at the exact same time. The nerve fibers 201 of FIG. 6 may be substantially similar to the nerve fibers 201 described herein with reference to FIG. 5.

The method 300 includes locating a first electrode 310 and a second electrode 312 along the nerve fibers 201 of a patient to capture the electrical activity propagating along the nerve fibers 201. The first electrode 310 is located closer to the central end 202 of the nerve fibers 201 than the second electrode 312. Conversely, the second electrode 312 is located closer to the peripheral end 204 of the nerve fibers 201 than the first electrode 310. The first electrode 310 and the second electrode 312 may be located on the same lead or on different leads and operably coupled to an IMD or components thereof.

The first electrode 310 and second electrode 312 may be operably coupled (e.g., electrically coupled) to a differentiation circuit 320 to differentiate between efferent and afferent components (e.g., a component of an IMD) via connections 311, 313, respectively. The differentiation circuit 320 may include a first amplifier 323 and a second amplifier 325, each having a first input operably coupled to one of the electrodes 310, 312 and a second input operably coupled to an electrical ground 321. The first electrode 310 is electrically coupled (e.g., as an input) to the first amplifier 323, and the second electrode 312 is electrically coupled (e.g., as an input) to the second amplifier 325. The differentiation circuit 320 may further include filtering circuitry to filter any undesired electrical activity from the electrical signals monitored by the first and second electrodes 310, 312.

When an electrical signal propagates in either direction along the nerve fibers 201, the first amplifier 323 outputs a positive waveform 322 and the second amplifier 325 outputs a positive waveform 324. The timing of the waveforms 322, 324 may be compared 326 e.g., to determine whether electrical activity is efferent or afferent, to determine the conduction velocity, etc., and the electrical signals may be integrated 328 similar to the integration 226 described herein with reference to FIG. 5 (e.g., the area under the curve for a period of time may be computed to generate a value).

Next, the method 300 may determine 330 whether the electrical signal that propagated along the nerve fibers 201 is efferent or afferent based on the timing comparison 326. For example, if the electrical activity monitored by the first electrode 310 (e.g. waveform 322) occurred before the electrical activity monitored by the second electrode 312 (e.g., waveform 324), then the monitored electrical activity propagated from the central end 202 to the peripheral end 204 of the nerve fibers 201, and therefore, the monitored electrical activity is efferent. Conversely, if the electrical activity monitored by the second electrode 312 (e.g., waveform 324) occurred before the electrical activity monitored by the first electrode 310 (e.g. waveform 322), then the monitored electrical activity propagated from the peripheral end 204 to the central end 202 of the nerve fibers 201 (in other words, from the right side of the figure to the left side), and therefore, the monitored electrical activity is afferent.

In other words, the timing difference of the action potential, or monitored electrical activity, between these two electrodes may be used to determine which direction the action potential propagates, e.g., if the electrode 310 detects the action potential earlier than electrode 312, the propagation occurs from central end to the peripheral end, and such propagation is assigned as including efferent components. Vice versa, if the electrode 312 detects the action potential earlier than electrode 310, the propagation is from the peripheral end to the central end, and such propagation is assigned as including afferent components. Often, due to the distance between the two electrodes being close, the velocity of nerve propagation being quick, and the use of a fast sampling rate, two connective action potentials monitored by the electrodes may overlap because the refractory period for nerves may be about 5 milliseconds to about 10 milliseconds.

Further, the unipolar recordings of method 300 may be used to determine action potential propagation velocity. For example, when the action potential propagates from central end 202, electrode 310 will detect the action potential first, followed by the detection of action potential by the electrode 312. A timing delay will exist between these two detections and the velocity of the action potential, or signal, is then determined by the time divided by the distance between these two electrodes.

Efferent and afferent signals traveling along nerve fibers 201 may also be differentiated by using processes (which, e.g., may be used in conjunction with the methods described herein) that take into account that fibers with different diameters and/or myelination (e.g., the thickness of the layer of myelin around the fiber) have different conduction velocities. For example, different classes and sub-classes (A-alpha, A-beta, A-gamma, A-delta, B, and C) of nerve fibers have different diameters and/or different levels of myelination. Further, each of the different types of fibers may conduct nerve signals corresponding to various functions of one or more physiological systems. As such, the conduction velocities, and thus the diameters, of the nerve fibers may be used to distinguish the different types of nerve signals being conducted over the nerve fibers. A-alpha fibers may have a diameter of about 12 to about 20 micrometers and a conduction velocity of about 70 meters per second to about 120 meters per second; A-beta fibers may have a diameter of about 5 micrometers to about 12 micrometers and a conduction velocity of about 30 meters per second to about 70 meters per second; A-gamma fibers may have a diameter of about 3 micrometers to about 6 micrometers and a conduction velocity of about 15 meters per second to about 30 meters per second; A-delta fibers may have a diameter of about 2 micrometers to about 5 micrometers and a conduction velocity of about 5 meters per second to about 30 meters per second; B fibers may have a diameter of about less than 3 micrometers and a conduction velocity of about 3 meters per second to about 15 meters per second; and C fibers may have a diameter of about 0.4 micrometers to about 1.2 micrometers and a conduction velocity of about 0.4 meters per second to about 2 meters per second.

For example, with respect to the vagus nerve, the A-alpha fibers of the vagus nerve may carry both efferent and afferent activity, e.g., related to somatic motor functionality and parasympathetic sensory functionality. Further, for example, A-beta fibers of the vagus nerve may carry afferent activity, the A-gamma fibers of the vagus nerve carry efferent activity, and the A-delta fibers of the vagus nerve may carry afferent activity. Still further, for example, the B fibers of the vagus nerve may carry efferent activity, e.g., related to parasympathetic motor functionality, and the C fibers of the vagus nerve may carry both efferent and afferent activity, e.g., related to parasympathetic sensory functionality and parasympathetic motor functionality.

In at least one embodiment, it may be expected (e.g., depending on the electrode locations, signal filtering techniques, etc.) that the efferent activity (e.g., electrical activity of the vagus nerve traveling towards the heart propagates over smaller, less myelinated fibers and that afferent activity (e.g., electrical activity of the vagus nerve traveling away from the heart) propagates over large, myelinated fibers. As described, smaller, less myelinated fibers conduct action potentials more slowly than large, myelinated fibers. As a result, efferent activity and afferent activity may be distinguished and identified using the monitored action potential's conduction velocity because efferent activity should travel slower than afferent activity.

In other words, the velocity of an action potential, or monitored electrical activity, calculated using the timing between the two electrodes 310, 312 may be used to determine which direction the action potential propagates, e.g., if the velocity of the action potential is slower than an efferent threshold value or is within a range of efferent values, then the propagation is occurring from central end 202 to the peripheral end 204, and such propagation is assigned as including efferent components. Vice versa, if the velocity of the action potential is faster than an afferent threshold value or is within a range of afferent values, then the propagation is occurring from the peripheral end 204 to the central end 202, and such propagation is assigned as including afferent components.

The nerve signal differentiation methods 200, 300 may be used in one or more therapy delivery methods (e.g., for adjustment of the therapy, initialization of the therapy, termination of the therapy, etc.). Further, the nerve signal differentiation methods as well as the other methods, systems, and devices herein may be used with any nerve signals of a patient (e.g., respiration nerve signals, muscle activity, etc.) and may be utilized in conjunction with any therapy, e.g., GI therapy (e.g., see FIG. 10), muscle therapy, etc.

Figure 7:
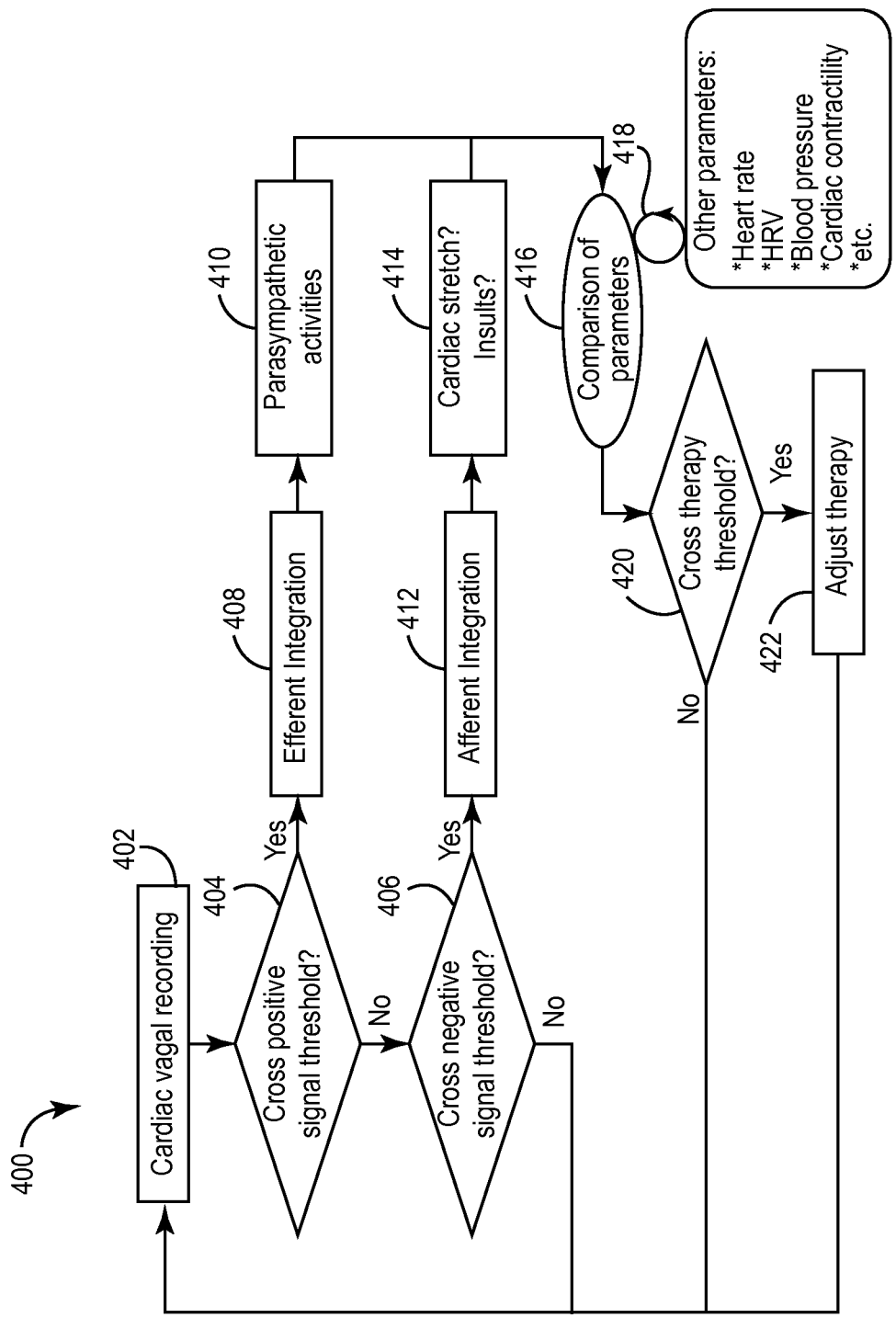
FIG. 7 is a flow chart of an exemplary method of nerve signal differentiation and cardiac therapy adjustment based on nerve signals.

For example, the efferent and afferent components of a patient's vagus nerve may be used in cardiac therapy. A flow chart illustrating an exemplary method 400 of nerve signal differentiation and cardiac therapy adjustment based on nerve signals is depicted in FIG. 7. The method 400 includes recording cardiac vagal signals 402 (e.g., the electrical activity of the patient's vagus nerve) with the systems and methods described herein, e.g., method 200 of FIG. 5.

Concurrently or periodically, the method 400 may determine whether the recorded cardiac vagal signals have crossed a positive signal threshold 404, which is similar to process step 228 described herein with reference to FIG. 5 except this system is configured such that positive electrical activity indicates efferent activity. The positive signal threshold may be a selected minimum value indicative of efferent integration (e.g., the positive signal threshold may be about two to about three times the baseline electrical activity the monitored nerve fibers). For example, if the recorded cardiac vagal signals exceed the positive signal threshold, then the recorded cardiac vagal signals may be efferent. In essence, the positive signal threshold may act to trigger further analysis of the presently recorded cardiac vagal signals for efferent components. Further, the positive signal threshold may also act as a filter, e.g., for filtering out undesired signals (e.g., too weak signals, signals operating at undesired frequencies, etc.).

Figure 8:
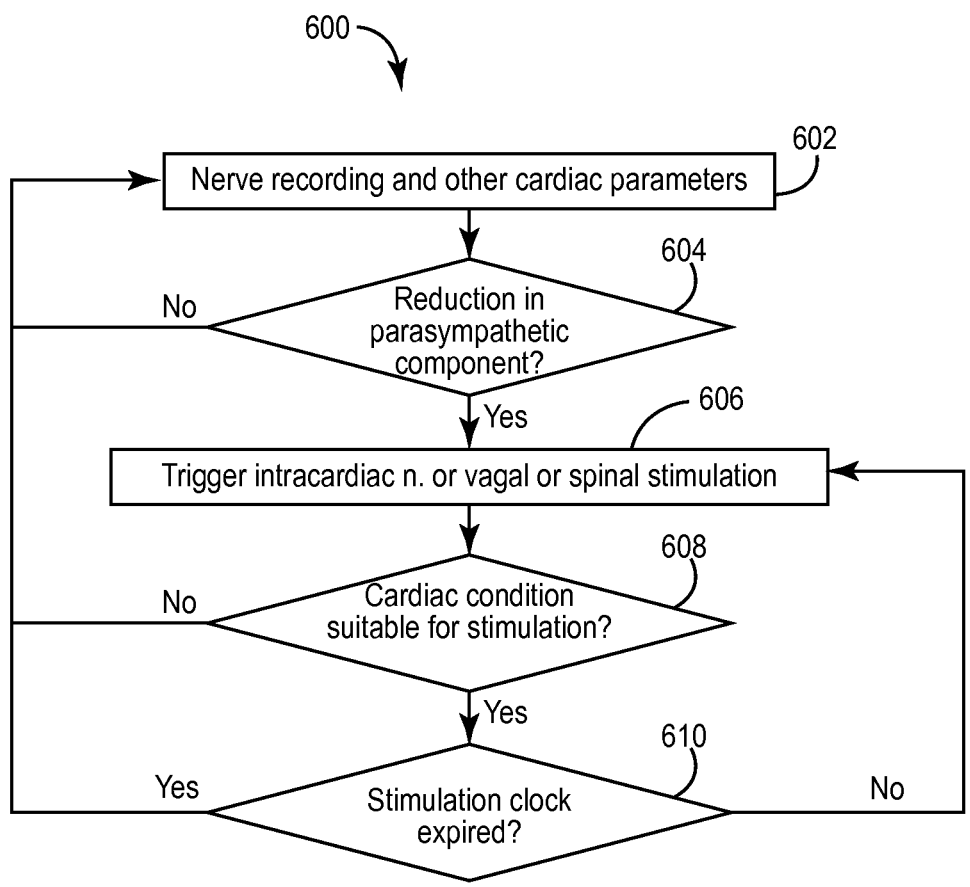
FIG. 8 is a flow chart of an exemplary method of initiating cardiac therapy based on nerve signals.

If it is determined that the recorded cardiac vagal signals have crossed a positive signal threshold 404, the method 400 may determine that the recorded cardiac vagal signals are efferent 408 similar to the processes of methods 200, 300 described herein with reference to FIGS. 7-8.

The method 400 may further determine whether the efferent components of the recorded cardiac signals include parasympathetic activity 410. For example, determining whether the efferent components of the recorded cardiac signals include parasympathetic activity 410 may include correlating the efferent components to a slowing heart rate, decreased HRV, prolonged R-R intervals, prolonged P-R intervals, etc. If the efferent components of the recorded cardiac signals are correlated to a slowing heart rate, decreased HRV, prolonged R-R intervals, prolonged P-R intervals, etc., it may be determined that the efferent components include parasympathetic activity. In the case of monitoring the electrical activity of the vagus nerve, the method 400 may assume that all efferent components are parasympathetic activity.

The method 400 may also determine whether the recorded cardiac vagal signals have crossed a negative signal threshold 406, which is similar to process step 228 described herein with reference to FIG. 5 except this system is configured such that negative electrical activity indicates afferent activity. Further, negative signal threshold step 406 may occur concurrently with process step 404 or after process step 404 (e.g., if it is determined that the recorded cardiac vagal signals have not crossed a positive signal threshold 404). The negative signal threshold may be a selected minimum value indicative of afferent integration (e.g., the magnitude of the negative signal threshold may be about two to about three times the baseline electrical activity the monitored nerve fibers). For example, if the recorded cardiac vagal signals exceed the negative signal threshold (i.e., less than the negative signal threshold), then the recorded cardiac vagal signals may be afferent. In essence, the negative signal threshold may act to trigger further analysis of the presently recorded cardiac vagal signals for afferent components. Further, the negative signal threshold may also act as a filter, e.g., for filtering out undesired signals (e.g., too weak signals, signals operating at undesired frequencies, etc.).

If it is determined that the recorded cardiac vagal signals have crossed a negative signal threshold 406, the method 400 may determine that the recorded cardiac vagal signals are afferent 412. Afferent components of the cardiac vagal signals may be indicative of some cardiac conditions, e.g., such as myocardial ischemia or insult like over-stretch. As such, method 400 may analyze the physiological parameters of the patient to determine if the patient is undergoing any particular cardiac conditions 414 (e.g., ischemia, overload, tissue inflammation, cardiac stretch, cardiac insults, etc.) that, e.g., may be related to the afferent signals detected. If it is determined that the recorded cardiac vagal signals have not crossed a negative signal threshold 406, the method 400 may return to recording cardiac vagal signals 402.

After determining that the recorded cardiac vagal signals include either parasympathetic activity 410 or activity indicative of certain cardiac conditions 414, the method 400 may conduct a comparison of physiological parameters 416 including the efferent signals and/or the afferent signals to determine whether the patient needs cardiac therapy, or in the case of ongoing cardiac therapy, needs an adjustment to the cardiac therapy. The physiological parameters may include the electrical activity of a patient's heart, chemical activity of a patient's heart, hemodynamic activity of a patient's heart, and electrical activity of the patient's vagus nerve as described herein.

Further, the physiological parameters may be compared to selected threshold values 420. For example, each physiological parameter may be compared to a specific selected threshold value that represents a point at which either cardiac therapy for a patient should be started, or in the case of ongoing cardiac therapy, the cardiac therapy should be adjusted. If it is determined that cardiac therapy does not need to be adjusted or started based on the comparison to selected threshold values, the method 400 may return to recording cardiac vagal signals 402.

If the comparison to selected threshold values determines that cardiac therapy needs be adjust or started, the method 400 may adjust (or start) the cardiac therapy 422. The cardiac therapy may include the delivery of vagal stimulation (e.g., electrical stimulation to a patient's vagus nerve), electrical stimulation for pacing the patient's heart 12 (e.g., bradycardia pacing, cardiac resynchronization therapy, anti-tachycardia pacing (ATP), high-energy shock pulses for cardioversion/defibrillation therapy, and/or other pacing therapies), etc.

For example, the patient's R-R intervals may be compared to selected threshold values indicative of healthy cardiac function and/or cardiac conditions. If it is determined that the patient's R-R intervals are indicative of unhealthy cardiac function and/or treatable cardiac conditions, then the cardiac therapy may need to be adjusted.

As described herein, cardiac therapy may be initiated and/or adjusted based on nerve signal recordings (e.g., the parasympathetic component of a nerve signal). An exemplary method 600 of initiating cardiac therapy based on nerve signals is depicted in FIG. 8. The method 600 may include data collection 602 (e.g., nerve recording and other cardiac parameters). Data collection 602 may include monitoring one or more physiological parameters of a patient, e.g., as described herein with reference to the IMD 10 of FIG. 1. Specifically, however, the data collection 602 includes monitoring nerve signals (e.g., of the vagus nerve). Although not shown, the method 600 may include the processes described herein, e.g., with reference to FIGS. 5-6, for identifying, processing, and/or filtering the efferent (or afferent) activity from the electrical activity of the nerve tissue (e.g., the vagus nerve).

Periodically or concurrently with the data collection 602, the method 600 includes determining whether the efferent activity of the electrical activity of the patient's vagus nerve is reduced 604. Determining whether the efferent activity of the electrical activity of the patient's vagus nerve is reduced 604 may be conducted using various processes. For example, the method may compare various parameters of the efferent activity to a selected value. Such parameters may include voltage, amplitude, frequency, pulses per heart beat, pulses per second, sum of integration, signal energy power of spectral analysis, timing of signals, and/or trend of nerve activity. The selected value may be a threshold representing the minimum or the maximum value of parasympathetic activity required for healthy cardiac function. In other words, if the patient's parasympathetic activity falls below a minimum selected value or exceeds a maximum selected value, it may be indicative of abnormal automatic nervous activities, unhealthy cardiac function, future cardiac conditions, and/or other organ problems. For example, the method may compare the pulses per second of the monitored efferent activity to a threshold value of about 3 pulses per second (e.g., the threshold value may be about 2 pulses per second to about 5 pulses per second depending on the patient, the physical activity of the patient, etc.). If the monitored efferent activity drops below 3 pulses per second, the method may determine that the efferent activity of the patient is reduced.

Further, for example, the method 600 may compare various parameters of the efferent activity presently being monitored or recorded to such parameters of efferent activity that have been previously recorded. Such parameters may include voltage, amplitude, frequency, pulses per heart beat, pulses per second, sum of integration, signal energy power using spectral analysis, timing of signals, and/or trend of nerve activity. In other words, the previously-monitored efferent activity may provide a baseline to which the presently-monitored efferent activity may be compared. If the presently-monitored efferent activity is less than the previously-monitored efferent activity (e.g., the previously-monitored efferent activity may have been analyzed and/or monitored previously), the presently-monitored efferent activity may be determined to be reduced, which therefore, may be indicative of abnormal automatic nervous activities, unhealthy cardiac function, risk of heart attack, future cardiac conditions, abnormal automatic activities to other organs like the GI system or somatic nerves to muscles.

Still further, for example, the method 600 may further identify, process, and/or filter the afferent activity/sympathetic activity from the electrical activity of the nerve tissue (e.g., the vagus nerve) and compare the efferent activity (and/or parasympathetic activity) of the electrical activity of the patient's vagus nerve to the afferent activity (and/or sympathetic activity) of the electrical activity of the patient's vagus nerve to determine if the efferent activity is reduced. Such comparison between efferent activity and afferent activity may compare various parameters (e.g., pulses per second), and further may not be a 1:1 comparison (e.g., each parameter may be multiplied, or transformed, for easier comparison).

In at least one embodiment, the amplitude (e.g., average amplitude over a selected time period) of a selected frequency range of the monitored efferent activity may be used to determine whether the efferent activity is reduced. For example, the method 600 may analyze the monitored efferent activity within the frequency spectrum to evaluate the amplitude in a selected frequency range (e.g., about 0.15 hertz to about 0.4 hertz, or high frequency (HF) band that, e.g., may be driven by respiration and may be derived mainly from vagal activity of the parasympathetic nervous system or about 0.04 hertz to about 0.15 hertz, or low frequency (LF) band that, e.g., may be derived from both parasympathetic and sympathetic activity and may reflect the delay in the baroreceptor loop), which is considered to purely reflect vagal activity. Further, the average amplitude of the selected frequency range of the presently-monitored efferent activity may be compared to a selected value or to the average amplitude of the selected frequency range of previously-monitored efferent activity to determine whether the efferent activity of the electrical activity of the at least one nerve fiber is reduced.

In at least another embodiment, the power spectrum of the selected frequency range of the monitored efferent activity may be used to determine whether the efferent activity is reduced. For example, the method 600 may calculate the power (e.g., average area under the curve over time) of the monitored efferent activity in the selected frequency range. Further, the average power of the selected frequency range of the presently-monitored efferent activity may be compared to a selected value or to the average power of the selected frequency range of previously-monitored efferent activity to determine whether the efferent activity of the electrical activity of the at least one nerve fiber is reduced.

Further, a relation may exist between the power spectra of the monitored nerve signals (e.g., of a selected frequency range (e.g., about 0.15 hertz to about 0.4 hertz) and the patient's HRV. Using such a relation or transfer function (e.g., which may be predetermined (e.g., using data from a plurality of patients), created using data from the present patient, etc.), a patient's nerve signals or the status thereof (e.g., the power spectra of the nerve signals) may be calculated using the monitored HRV of the patient. In other words, a function may be provided (e.g., predetermined, calculated for a specific patient, etc.) relating the status of the patient's vagus nerve to the electrical activity of the patient's heart (e.g., the HRV of the electrical activity of the patient's heart) for use in therapy, assessing a status of the patient's vagus nerve using the monitored electrical activity of the patient's heart using the function, and initiating or adjusting cardiac therapy to the patient based on the assessed status of the patient's vagus nerve.

Further, in at least one embodiment, a comparison between efferent activity in general, average activity within a certain phase of the cardiac cycle, or efferent activity within a certain frequency band (e.g., HF or LF) may provide information about the intactness of the nerves innervating the heart. This could be indicative of nerve deterioration in certain cases, e.g., diabetes or cardiac infarct.

If it has been determined that there has not been a reduction in the parasympathetic component 604, then the method 600 may return to data collection 602. If it has been determined that there has been a reduction in the parasympathetic component 604, then the method 600 may initiate the delivery of cardiac therapy 606. Such therapy may include delivering vagal stimulation (e.g., electrical stimulation to a patient's vagus nerve), electrical stimulation for pacing the patient's heart 12 (e.g., bradycardia pacing, cardiac resynchronization therapy, ATP, and/or other pacing therapies), and/or other types of therapy like neuromodulation (e.g., spinal cord stimulation), etc. Further, in at least one embodiment, an IMD may be capable of delivering high-energy shock pulses for cardioversion/defibrillation therapy delivered in response to, e.g., tachycardia detections.

Further, the cardiac therapy may be delivered during or after the monitored nerve signals. For example, if the method is delivering vagal stimulation, the vagal stimulation may be delivered after a monitored burst of efferent and/or parasympathetic activity (e.g., vagal burst discharges) in order to, e.g., expand vagal excitation and effect. The cardiac therapy may start before the burst of nerve activity ceases or may start after the nerve activity ceases. For example, the method may deliver vagal stimulation for a selected period of time after a burst of efferent activity ceases.

After or during the delivery of cardiac stimulation 606, the method 600 may determine whether the patient's cardiac condition is suitable for cardiac stimulation 608. Determining whether the patient's cardiac condition is suitable for cardiac stimulation 608 may utilize the monitored physiological parameters (e.g., the electrical activity, chemical activity, hemodynamic information, and/or nerve activity of the patient's heart).

If it is determined that the patient's cardiac condition is not suitable for cardiac stimulation, the method 600 may return to data collection 602. For example, determining whether the patient's cardiac condition is suitable for cardiac stimulation 608 may include analyzing the monitored physiological parameters for termination criteria. Analyzing such monitored physiological parameters may include determining whether the electrical activity of the patient's heart indicates a ventricular arrhythmia, determining whether the R-R intervals have not increased, and determining whether the P-R intervals have not increased. The method may then terminate the delivery of electrical stimulation to the vagus nerve if either the electrical activity of the patient's heart indicates a ventricular arrhythmia, the R-R intervals have not increased, or the P-R intervals have not increased.

Further, for example, the method may include determining whether the patient's cardiac condition is worsening after the delivery of electrical stimulation to the patient's vagus nerve and terminating the delivery of electrical stimulation to the patient's vagus nerve if the patient's cardiac condition is worsening.

More details of methods of and devices for use in treating patients (e.g., using vagal stimulation) are described, e.g., in U.S. patent application entitled "VAGAL STIMULATION" to Ziegler et al., U.S. patent application Ser. No. 12/770,161 entitled "TERMINATION CRITERIA FOR VAGAL STIMULATION" to Kornet et al., U.S. patent application Ser. No. 12/770,090 entitled "VAGAL STIMULATION FOR ARRHYTHMIA PREVENTION" to Zhou et al., U.S. patent application Ser. No. 12/770,143 entitled "REGULATION OF PRELOAD" to Cornelussen et al., U.S. patent application Ser. No. 12/770,121 entitled "VAGAL STIMULATION FOR TREATING MYOCARDIAL INFARCTION" to Zhou et al., U.S. patent application Ser. No. 12/770,227 entitled "NERVE SIGNAL DIFFERENTIATION" to Zhou et al. which was converted to U.S. Provisional Patent Application Ser. No. 61/397,703, and U.S. Provisional Pat. App. No. 61/329,374 entitled "THERAPY USING PERTURBATION AND EFFECT OF PHYSIOLOGICAL SYSTEMS" to John Burnes et al., each of which were filed on the same date as the present application and are incorporated herein by reference in their entirety.

If it is determined that the patient's cardiac condition is suitable for cardiac stimulation, the method 600 may determine whether a stimulation clock (e.g., a timer that was started when the cardiac stimulation started) has expired 610. If the stimulation clock 610 has expired, the method 600 may return to data collection 602. If the stimulation clock has not expired, the method 600 may return to delivering cardiac stimulation 606. In at least one embodiment, the stimulation clock runs for about, e.g., 30 or 45 seconds. In other words, the method may terminate the delivery of electrical stimulation to the patient's vagus nerve after a selected time period has elapsed after the initiation of the delivery of electrical stimulation.

Figure 9:
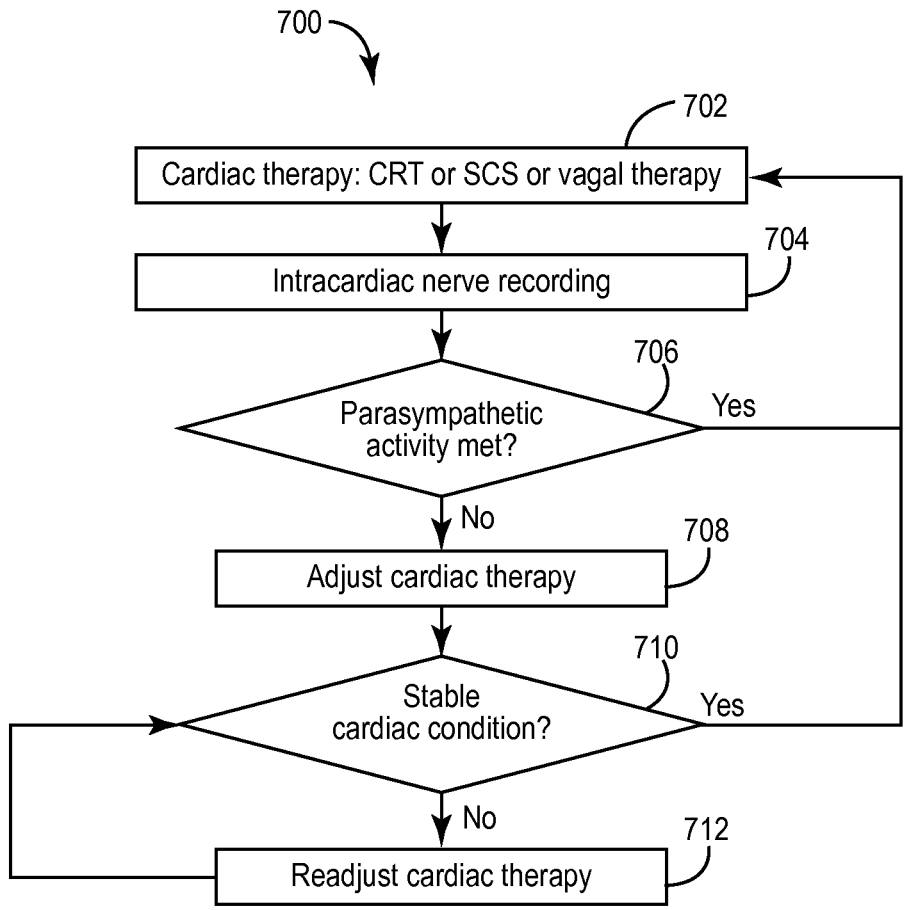
FIG. 9 is a flow chart of an exemplary method of adjusting cardiac therapy based on nerve signals.

A flow chart illustrating an exemplary method 700 of adjusting cardiac therapy based on nerve signals is depicted in FIG. 9. The method 700 includes delivering cardiac therapy 702, e.g., vagal stimulation, cardiac resynchronization therapy, and/or spinal cord stimulation. The delivering of cardiac therapy 702 may be substantially similar to the delivery of cardiac therapy 606 described herein with reference to FIG. 8.

Periodically or concurrently with the delivery of cardiac therapy 702, the method 700 may record, or monitor, intracardiac nerve signals 704 (e.g., of the vagus nerve). Although not shown, the method 600 may include the processes described herein, e.g., with reference to FIGS. 5-6, for identifying, processing, and/or filtering efferent and/or afferent activity from the electrical activity of the nerve tissue (e.g., the vagus nerve).

Using the monitored nerve signals, the method 700 may determine whether to the parasympathetic activity of the nerve signals has been met 706. In other words, the method 700 may include analyzing the monitored physiological parameters 706 after delivering cardiac therapy 702. Such analyzing monitored physiological parameters may include determining whether the efferent activity of the electrical activity of the patient's vagus nerve is reduced. The processes in method 700 for determining whether the efferent activity of the electrical activity of the patient's vagus nerve is reduced may be similar to the processes described in method 600 of FIG. 8.

If the parasympathetic activity of the nerve signals has been met, then the method 700 may return to delivering cardiac therapy 702. If the parasympathetic activity of the nerve signals has not been met, then the method 700 may adjust the cardiac therapy 708. In other words, the method 700 may adjust the cardiac therapy if the efferent activity of the electrical activity of the patient's vagus nerve is reduced. Adjusting the cardiac therapy 708 may include adjusting the voltage, amplitude, number of pulses per burst, burst frequency, pulse frequency, and pulse width of pacing or burst pacing therapy. Further, adjusting the cardiac therapy 708 may include triggering other neuromodulation therapy (e.g., spinal cord stimulation), drug pumps, or alerts to a patient to take medicine or rest (e.g., via telemetry). In at least one embodiment, adjusting the cardiac therapy may include determining if the vagal efferent components (e.g., sympathetic) are too high and delivering high frequency electrical pulses to the corresponding nerve through the same recording electrodes or different electrodes to block nerve conduction to, e.g., reduce the over-excited nerve activities.

If the cardiac therapy includes vagal stimulation, the parameters of such vagal simulation may be adjusted within certain ranges. Such parameters may include time (e.g., the vagal stimulation may be delivered for a selected time period), voltage (e.g., within a range of about 1 volt and about 8 volts), frequency of the pulses within a burst of pulses (e.g., within a range of about 1 hertz to about 150 hertz), frequency of the bursts (e.g., within a range of about 5 hertz to about 100 hertz), synchronization (e.g., with different portions of the electrical activity of the patient's heart), pulse width of each pulse (e.g., within a range of about 0.1 milliseconds to about 1 milliseconds), and number of pulses per burst (e.g., within a range of about 3 pulses to about 20 pulses), etc.

After the cardiac therapy has been adjusted, the method 700 may determine whether the patient has a stable cardiac condition 710, e.g., using electrical activity, chemical activity, and/or hemodynamic activity of the patient's heart. Determining whether the patient has stable cardiac condition 710 may be substantially similar to determining whether the patient's cardiac condition is suitable for cardiac stimulation 608 as described herein with reference to FIG. 8.

If it is determined that the patient has a stable cardiac condition, the method 700 may return to delivering cardiac therapy 702. If it is determined that the patient does not have stable cardiac condition, the method 700 may readjust the cardiac therapy 712, which may be substantially similar to adjusting cardiac therapy 708. After the cardiac therapy has been readjusted 712, the method 700 may again determine whether the patient has a stable cardiac condition 710.

Although methods 600, 700 are focused on cardiac therapy based on nerve activity, such methods are not limited to the delivery of cardiac therapy and may be used to treat other various conditions. For example, such methods may be used to treat and monitor organ functions in, e.g., the GI system, the bladder, various muscles, glands (e.g., for releasing hormones), etc.

One example where nerve recording and/or stimulation may be useful can be found in the GI system. The splanchnic nerves are paired nerves that contribute to the innervation of the viscera and carry fibers of the autonomic nervous system (efferent fibers) as well as sensory fibers from the organs (afferent fibers). One function of the splanchnic nerves is to regulate intestinal function. During proper functional digestion, sensors are stimulated in the intestine when food is moved into the intestine thereby triggering secretion of digestive enzymes and slowing contraction of intestinal muscles. As such, the sensing and stimulation of splanchnic nerves may help to regulate intestinal digestion.

Another function of the splanchnic nerves is to regulate bowel movements. When urine accumulates in bladder, sensors in bladder are stimulated by stretching and signals are propagated from such sensor to the spine and brain. Subsequently, efferent activity propagates from the brain to the bladder to trigger urination. If such efferent activity does not occur, the patient may not be able to urinate properly. As such, the sensing and stimulation of splanchnic nerves may help to regulate urination or other bowel movements.

In at least another embodiment, in the GI system, if the parasympathetic components of the autonomic nerves are too low, the GI system may, as described herein, not function appropriately, thus electrical stimulation of certain nerves (e.g., splanchnic nerves) may be triggered to increase parasympathetic tone for digestion and improve GI function. An example of a method of using nerve signals to deliver therapy to treat the GI system is described herein with reference to FIG. 10.

Figure 10:
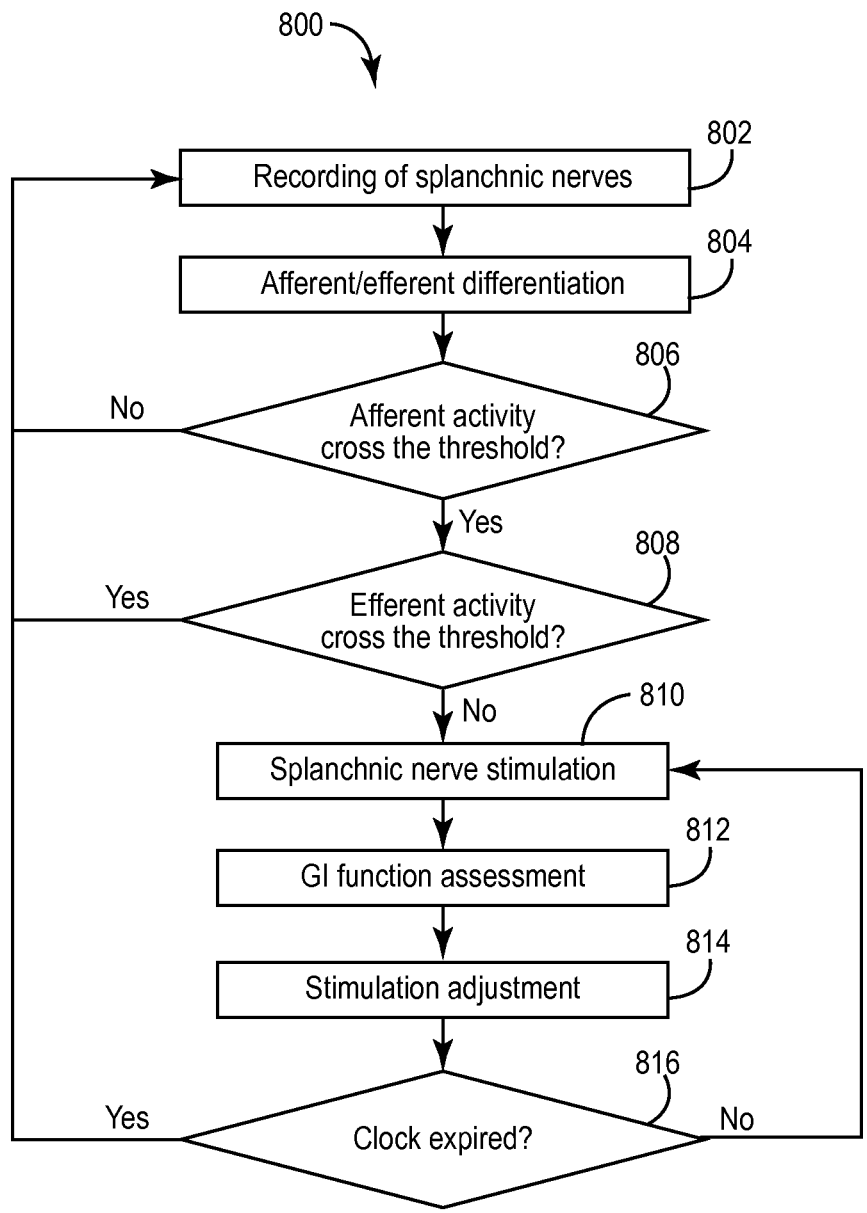
FIG. 10 is a flow chart of an exemplary method of delivering and adjusting gastrointestinal therapy based on nerve signals.

A flow chart illustrating an exemplary method 800 of delivering and adjusting GI therapy based on nerve signals is depicted in FIG. 10. The method 800 includes data collection 802, which may include monitoring one or more physiological parameters of a patient, e.g., as described herein with reference to the IMD 10 of FIG. 1. Specifically, however, the data collection 802 includes monitoring nerve signals of the splanchnic nerves. The method 800 may further include the processes described herein, e.g., with reference to FIGS. 5-6, for differentiating the efferent activity from the afferent activity within the electrical activity of the nerve tissue (e.g., the splanchnic nerves) 804.

Periodically or concurrently with the data collection 802 and afferent/efferent differentiation 804, the method 800 includes determining whether the afferent activity of the electrical activity of the patient's splanchnic nerves crosses a threshold 806. Determining whether the afferent activity of the electrical activity of the patient's splanchnic nerves crosses a threshold value 806 may be conducted using various processes. For example, the method 800 may compare various parameters of the afferent activity to a selected threshold value. Such parameters may include voltage, amplitude, frequency, pulses per second, sum of integration, signal energy power of spectral analysis, timing of signals, and/or trend of nerve activity. The selected threshold value may be a threshold representing the minimum value of afferent activity required to indicate that food is located in the intestine. In other words, if the patient's afferent activity is above the selected threshold value, food may be present in the intestine, and conversely, if the patient's afferent activity is below the selected value, no food may be present in the intestine.

If the afferent activity of the splanchnic nerves crosses the threshold value, then the method 800 may determine if the efferent activity of the splanchnic nerves crosses another threshold value 808. Such threshold determination may be similar to process step 806 for afferent activity but the threshold value 808 may be indicative of the minimum value required for proper digestive function in response to food being located in the intestine. If the patient's efferent activity is above the selected threshold value, then the body is responding effectively (e.g., delivering nerve signals to triggering secretion of digestive enzymes and slowing contraction of intestinal muscles) and the method 600 may return to data collection 802. Conversely, if the patient's efferent activity is below the selected value, then the method 800 may deliver GI therapy 810, e.g., electrical stimulation of the splanchnic nerve, which may be similar to the nerve stimulation 606 described herein with reference to FIG. 8.

After the GI therapy 810, the method 800 may assess the functionality of the patient's GI system 812. Assessing the functionality of the patient's GI system 812 may include analyzing the monitored one or more physiological parameters, e.g., analyzing the electrical activity (efferent and/or afferent activity) of the splanchnic nerves. For example, if the efferent activity of the splanchnic nerves is still below the selected threshold value as utilized in process step 808, then it may be determined that the GI therapy (e.g., splanchnic nerve stimulation) may need to be adjusted.

Adjusting the splanchnic nerve stimulation 814 may include adjusting the voltage, amplitude, number of pulses per burst, burst frequency, pulse frequency, and pulse width of pacing or burst pacing therapy, etc. For example, if it is determined that the efferent activity of the patient's splanchnic nerves is still too low, the method may supplement the efferent activity by delivering stimulation to the splanchnic nerves for a selected period of time after the efferent activity has ceased.

The method 800 may further determine whether a stimulation clock (e.g., a timer that was started when the GI therapy started) has expired 816. If the stimulation clock 816 has expired, the method 800 may return to data collection 802. If the stimulation clock has not expired, the method 800 may return to delivering GI therapy 810. In at least one embodiment, the stimulation clock runs for about, e.g., 30 or 45 seconds. In other words, the method may terminate the delivery of GI therapy after a selected time period has elapsed after the initiation of the delivery of GI therapy.

One example of a medical device that may be used in carrying out the methods described herein for providing treatment is depicted in FIG. 1 as a schematic diagram of an implantable medical device (IMD).

The IMD 10 may be configured to monitor one or more physiological parameters of a patient (e.g., electrical activity of a patient's heart, chemical activity of a patient's heart, hemodynamic activity of a patient's heart, and electrical activity of the patient nerves). Although the IMD 10 has shown is configured to monitor the patient's heart, IMD 10 or similar devices may used for monitoring and delivering therapy to any organs or parts of a patient. In this example, the monitored physiological parameters, in turn, may be used by the IMD to detect various cardiac conditions, e.g., ventricular tachycardia (VT), ventricular fibrillation (VF), supraventricular ventricular tachycardia (SVT), atrial fibrillation (AF), atrial tachycardia (AT), ischemia/infarction, heart failure, etc., and to treat such cardiac conditions with therapy. Such therapy may include delivering vagal stimulation (e.g., electrical stimulation to a patient's vagus nerve), electrical stimulation for pacing the patient's heart 12 (e.g., bradycardia pacing, cardiac resynchronization therapy, ATP, and/or other pacing therapies), etc. Further, in at least one embodiment, the IMD 10 may be capable of delivering high-energy shock pulses for cardioversion/defibrillation therapy delivered in response to, e.g., tachycardia detections.

As used herein, "stimulation of the vagus nerve," also referred to herein simply as "vagal stimulation," refers to stimulation of neural tissue innervating the myocardium, directly or indirectly, e.g., stimulation of one or more of the vagus nerve or its branches (e.g., including the afferent and/or efferent fibers), the sinoatrial (SA) nodal fatty pad, the atrioventricular (AV) nodal fatty pad and along the great vein, the cervical vagus nerve (e.g., the right or left side), the fat pad located between the medial superior vena cava and aortic root (SVC-Ao fat pad), the fat pad superior to the right pulmonary artery, the fat pad at the IVC-left atrial junction (IVC-LA fat pad), the fat pad proximate the right pulmonary vein-atrial junction (RPV fat pad), the spinal cord (e.g., vertebral levels T1-T12, C1-C8, etc. such as described in U.S. Pat. App. Pub. No. 2002/0107552 A1 to Hill et al., which is incorporated herein by reference in its entirety), and additional intracardiac locations near the SA node, AV node, coronary sinus, and base of right ventricle.

Figure 11:
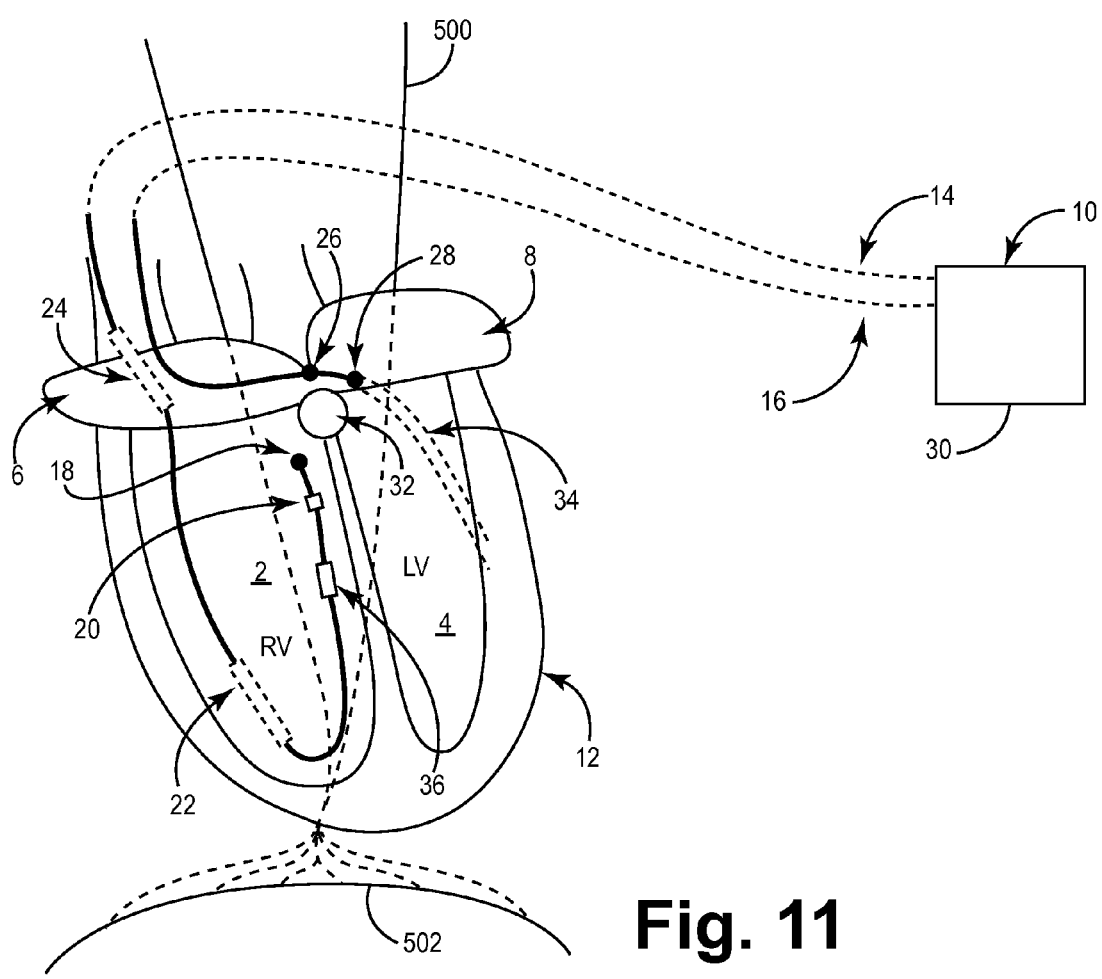
FIG. 11 is a schematic diagram of an implantable medical device (IMD) operably coupled to a patient's heart and diaphragm.

One or more other embodiments of the present disclosure relates to sensing and stimulating a phrenic nerve of a heart failure patient with sleep apnea. In one or more embodiments, the LV lead 16 is placed in, around or near the phrenic nerve 500 that runs behind the left ventricle, as shown in FIG. 11. The phrenic nerve 500 descends obliquely with the internal jugular vein (IJV) across the anterior scalene, deep to the prevertebral layer of deep cervical fascia and the transverse cervical and suprascapular arteries. Found in the middle mediastinum, both the left and right phrenic nerves run from C3, C4 and C5 along the anterior scalene muscle deep to the carotid sheath. The right phrenic nerve passes over the brachiocephalic artery, posterior to the subclavian vein, and then crosses the root of the right lung anteriorly and then leaves the thorax by passing through the vena cava hiatus opening in the diaphragm at the level of T8. The right phrenic nerve passes over the right atrium. The left phrenic nerve passes over the pericardium of the left ventricle and pierces the diaphragm separately. The LV lead 16 can be placed around or near the left phrenic nerve. For example, the LV lead 16 can be placed within a few millimeters (mm) (e.g. about 5 mm or less than 5 mm) of the left phrenic nerve 500.

After the LV lead has been properly placed, the therapy system or IMD 10 can monitor physiological conditions such as electrical activities from the phrenic nerve. By monitoring phrenic nerve activities and distinguishing the afferent/efferent nerve activities, as previously described, the IMD 10 can determine when and what electrical stimulation parameters to use during electrical stimulation to the phrenic nerve. For example, efferent components of phrenic nerve activity should have a certain burst frequency (e.g. 5 to 10 nerve discharges per burst, 12-16 bursts per minute) and magnitude (5-20 microvolts). When efferent components are weak (e.g. nerve discharge per second is 5 Hertz), especially in conjunction with too slow respiration (e.g. less than about 10 respirations per minute) and/or weak respiratory volume (e.g. about 500-800 milliliters per respiration cycle) relative to diaphragm 502, IMD 10 then initiates or delivers electrical stimulation to the phrenic nerve 500 with a defined amplitude (e.g. 1-8 volts) and frequency (e.g. 10-20 Hertz per burst, 12 to 14 burst rate per minute, etc.), to modulate respiration rate and volume.

Alternatively, IMD 10 can detect a pattern of phrenic nerve 500 activities to determine whether there is sleep apnea characterized by irregularity in respiration rhythm and magnitude. Once detected, IMD 10 can deliver electrical stimulation to the phrenic nerve 500 via the LV lead 16 to correct sleep apnea, especially when the sleep apnea pattern is detected in conjunction with the occurrence of heart failure decompensation, the latter can be detected via Medtronic Optivol or pressure monitoring. IMD 10 then checks to verify that, for example, respiration rate has returned to a normal rate (e.g. 12-14 respiration per minute) or a normal rate for that specific patient. A patient with heart failure may not be able to achieve a normal respiration rate; however, as long as the patient's respiration rate is substantially improved (e.g. +/−a few respiration cycles from the previous state) through electrical stimulation, the IMD 10 may be deemed to achieved a desired result.

Skilled artisans appreciate that ranges provided herein for phrenic nerve stimulation are designated for adults and the ranges may be adjusted for other conditions (e.g. age of the patient or other factors). Additionally, it is appreciated that the LV lead 16 may be placed near both the phrenic nerve and the vagus nerve.

The methods described herein are intended to illustrate the general functional operation of the devices and/or systems described herein, and should not be construed as reflective of a specific form of software or hardware necessary to practice one or more of the methods described herein. It is believed that the particular form of software will be determined primarily by the particular system architecture employed in a device (e.g., an implantable medical device) and/or system and by the particular detection and therapy delivery methodologies employed by the device and/or system. Providing software to accomplish the described methods in the context of any modern implantable medical device, given the disclosure herein, is within the abilities of one of skill in the art.

Further, methods described in conjunction with flow charts presented herein may be implemented in a computer-readable medium that includes computer instructions or software for causing a programmable processor to carry out the methods described. Computer instructions are typically stored in a "computer-readable medium" such as random access memory (RAM). "Computer-readable medium" includes but is not limited to any volatile or non-volatile media, such as a RAM, read only memory (ROM), non-volatile random access memory (NVRAM), electrically erasable programmable read-only memory (EEPROM), compact disc read-only memory (CD-ROM)), flash memory, and the like. The instructions may be implemented as one or more software modules, which may be executed by themselves or in combination with other software.

The hardware used to the accomplish the described methods, may include any one or more of a microprocessor, a digital signal processor (DSP), a controller, an application specific integrated circuit (ASIC), a field programmable gate array (FPGA), or equivalent discrete or integrated logic circuitry. In one or more exemplary embodiments, the processor may include multiple components, such as any combination of one or more microprocessors, one or more controllers, one or more DSPs, one or more ASICs, or one or more FPGAs, as well as other discrete or integrated logic circuitry. The functions and processes described herein may be embodied as software, firmware, hardware, or any combination thereof. As used herein, the term "circuitry" may be implemented in software as executed by one or more processes, firmware, hardware, or any combination thereof.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. An implantable medical device for delivering cardiac therapy comprising:
   monitoring apparatus configured to monitor physiological parameters of a patient, wherein the monitoring apparatus comprises at least two electrodes configured to monitor electrical activity of the patient's vagus nerve;
   a sensing module operably coupled to the monitoring apparatus and configured to receive the monitored physiological parameters;
   a therapy delivery module configured to deliver cardiac therapy to the patient;
   control module operably coupled to the sensing module and to the therapy delivery module and configured to:
   differentiate between efferent activity and afferent activity of the monitored electrical activity of the patient's vagus nerve,
   analyze the monitored physiological parameters by at least determining whether the efferent activity of the electrical activity of the patient's vagus nerve is reduced over time, and
   initiate or adjust cardiac therapy to the patient if the efferent activity of the electrical activity of the patient's vagus nerve is reduced, wherein the control module is further configured to:
   determine whether the monitored electrical activity of the patient's vagus nerve comprises afferent activity, and
   determine whether the efferent activity of the electrical activity of the patient's vagus nerve is reduced by at least comparing the efferent activity to the afferent activity.

2. An implantable medical device for delivering cardiac therapy comprising:
   monitoring apparatus configured to monitor physiological parameters of a patient, wherein the monitoring apparatus comprises at least two electrodes configured to monitor electrical activity of the patient's vagus nerve;
   a sensing module operably coupled to the monitoring apparatus and configured to receive the monitored physiological parameters;
   a therapy delivery module configured to deliver cardiac therapy to the patient;
   control module operably coupled to the sensing module and to the therapy delivery module and configured to:
   differentiate between efferent activity and afferent activity of the monitored electrical activity of the patient's vagus nerve,
   analyze the monitored physiological parameters by at least determining whether the efferent activity of the electrical activity of the patient's vagus nerve is reduced over time, and
   initiate or adjust cardiac therapy to the patient if the efferent activity of the electrical activity of the patient's vagus nerve is reduced, wherein the control module is configured to determine whether the efferent activity of the electrical activity of the patient's vagus nerve is reduced by at least comparing the average amplitude of a selected frequency range of the efferent activity to a selected value.

3. An implantable medical device for delivering cardiac therapy comprising:
   monitoring apparatus configured to monitor physiological parameters of a patient, wherein the monitoring apparatus comprises at least two electrodes configured to monitor electrical activity of the patient's vagus nerve;

a sensing module operably coupled to the monitoring apparatus and configured to receive the monitored physiological parameters;

a therapy delivery module configured to deliver cardiac therapy to the patient;

control module operably coupled to the sensing module and to the therapy delivery module and configured to:

differentiate between efferent activity and afferent activity of the monitored electrical activity of the patient's vagus nerve, analyze the monitored physiological parameters by at least determining whether the efferent activity of the electrical activity of the patient's vagus nerve is reduced over time, and initiate or adjust cardiac therapy to the patient if the efferent activity of the electrical activity of the patient's vagus nerve is reduced, wherein the control module is configured to determine whether the efferent activity of the electrical activity of the patient's vagus nerve is reduced by at least comparing the average amplitude of a selected frequency range of the presently-monitored efferent activity to the average amplitude of the selected frequency range of previously-monitored efferent activity.

4. An implantable medical device for delivering cardiac therapy comprising:

monitoring apparatus configured to monitor physiological parameters of a patient, wherein the monitoring apparatus comprises at least two electrodes configured to monitor electrical activity of the patient's vagus nerve;

a sensing module operably coupled to the monitoring apparatus and configured to receive the monitored physiological parameters;

a therapy delivery module configured to deliver cardiac therapy to the patient;

control module operably coupled to the sensing module and to the therapy delivery module and configured to:

differentiate between efferent activity and afferent activity of the monitored electrical activity of the patient's vagus nerve, analyze the monitored physiological parameters by at least determining whether the efferent activity of the electrical activity of the patient's vagus nerve is reduced over time, and initiate or adjust cardiac therapy to the patient if the efferent activity of the electrical activity of the patient's vagus nerve is reduced, wherein the control module is configured to determine whether the efferent activity of the electrical activity of the patient's vagus nerve is reduced by at least comparing the average power of a selected frequency range of the efferent activity to a selected value.

5. An implantable medical device for delivering cardiac therapy comprising:

monitoring apparatus configured to monitor physiological parameters of a patient, wherein the monitoring apparatus comprises at least two electrodes configured to monitor electrical activity of the patient's vagus nerve;

a sensing module operably coupled to the monitoring apparatus and configured to receive the monitored physiological parameters;

a therapy delivery module configured to deliver cardiac therapy to the patient;

control module operably coupled to the sensing module and to the therapy delivery module and configured to:

differentiate between efferent activity and afferent activity of the monitored electrical activity of the patient's vagus nerve, analyze the monitored physiological parameters by at least determining whether the efferent activity of the electrical activity of the patient's vagus nerve is reduced over time, and initiate or adjust cardiac therapy to the patient if the efferent activity of the electrical activity of the patient's vagus nerve is reduced, wherein the control module is configured to determine whether the efferent activity of the electrical activity of the patient's vagus nerve is reduced by at least comparing the average power of a selected frequency range of the presently-monitored efferent activity to the average power of the selected frequency range of previously-monitored efferent activity.

* * * * *